US010717659B2

(12) United States Patent
Dobrinsky

(10) Patent No.: US 10,717,659 B2
(45) Date of Patent: Jul. 21, 2020

(54) ULTRAVIOLET IRRADIATION OF AQUATIC ENVIRONMENT

(71) Applicant: Sensor Electronic Technology, Inc., Columbia, SC (US)

(72) Inventor: Alexander Dobrinsky, Silver Spring, MD (US)

(73) Assignee: Sensor Electronic Technology, Inc., Columbia, SC (US)

(*) Notice: Subject to any disclaimer, the term of this patent is extended or adjusted under 35 U.S.C. 154(b) by 0 days.

(21) Appl. No.: 16/144,350

(22) Filed: Sep. 27, 2018

(65) Prior Publication Data

US 2019/0100445 A1 Apr. 4, 2019

Related U.S. Application Data

(60) Provisional application No. 62/566,425, filed on Sep. 30, 2017.

(51) Int. Cl.
*C02F 1/32* (2006.01)
*A61L 2/23* (2006.01)
*A61L 2/10* (2006.01)

(52) U.S. Cl.
CPC .......... *C02F 1/32* (2013.01); *A61L 2/10* (2013.01); *A61L 2/23* (2013.01); *C02F 1/325* (2013.01); *C02F 2201/326* (2013.01); *C02F 2201/3221* (2013.01); *C02F 2201/3228* (2013.01); *C02F 2209/06* (2013.01); *C02F 2209/29* (2013.01);
(Continued)

(58) Field of Classification Search
CPC .......... C02F 1/32; C02F 2201/3221; C02F 2305/10; C02F 1/325; C02F 2201/3227; A61L 2/10; A61L 2/24; A61L 2/0047; A01K 63/045; A01K 63/04; A01K 63/006; A01K 63/047; A01K 63/003
See application file for complete search history.

(56) References Cited

U.S. PATENT DOCUMENTS 3,971,338 A * 7/1976 Alexson ................. A01K 63/04
 119/262
3,971,947 A * 7/1976 Lambert ................ A01K 63/04
 250/437

(Continued)

*Primary Examiner* — Brooke Purinton
(74) *Attorney, Agent, or Firm* — LaBatt, LLC

(57) ABSTRACT

Ultraviolet irradiation of an aquatic environment for the purposes of sterilization, disinfection, and/or cleaning fluids and surfaces associated with the aquatic environment. The aquatic environment can be irradiated using an ultraviolet illuminator having at least one ultraviolet radiation source and at least one sensor to detect conditions of the aquatic environment including fluid conditions and/or surface conditions associated with the aquatic environment. A control unit, operatively coupled to the at least one ultraviolet radiation source and the at least one sensor, determines a presence of algae growth about the aquatic environment. The control unit is further configured to direct the at least one ultraviolet radiation source to irradiate the aquatic environment at locations where there is a presence of algae growth for removal and suppression of further growth, monitor the irradiation with the at least one sensor, and adjust irradiation parameters as a function of detected conditions.

20 Claims, 9 Drawing Sheets

(52) U.S. Cl.
CPC ...... *C02F 2209/36* (2013.01); *C02F 2305/10* (2013.01)

(56) References Cited

U.S. PATENT DOCUMENTS

| | | | | |
|---|---|---|---|---|
| 5,054,424 | A * | 10/1991 | Sy | A01K 63/045 119/231 |
| 5,901,663 | A * | 5/1999 | Reinke | A01K 63/047 119/259 |
| 6,086,760 | A * | 7/2000 | Hoffa | A01K 63/04 119/264 |
| 7,553,456 | B2 | 6/2009 | Gaska et al. | |
| 7,634,996 | B2 | 12/2009 | Gaska et al. | |
| 8,277,734 | B2 | 10/2012 | Koudymov et al. | |
| 8,980,178 | B2 | 3/2015 | Gaska et al. | |
| 9,006,680 | B2 | 4/2015 | Bettles et al. | |
| 9,034,271 | B2 | 5/2015 | Shur et al. | |
| 9,061,082 | B2 | 6/2015 | Gaska et al. | |
| 9,138,499 | B2 | 9/2015 | Bettles et al. | |
| 9,179,703 | B2 | 11/2015 | Shur et al. | |
| 9,572,903 | B2 | 2/2017 | Dobrinsky et al. | |
| 9,603,960 | B2 | 3/2017 | Dobrinsky et al. | |
| 9,687,577 | B2 | 6/2017 | Dobrinsky et al. | |
| 9,707,307 | B2 | 7/2017 | Shur et al. | |
| 9,718,706 | B2 | 8/2017 | Smetona et al. | |
| 9,724,441 | B2 | 8/2017 | Shur et al. | |
| 9,750,830 | B2 | 9/2017 | Shur et al. | |
| 9,757,486 | B2 | 9/2017 | Dobrinsky et al. | |
| 9,795,699 | B2 | 10/2017 | Shur et al. | |
| 9,801,965 | B2 | 10/2017 | Bettles et al. | |
| 9,802,840 | B2 | 10/2017 | Shturm et al. | |
| 9,878,061 | B2 | 1/2018 | Shur et al. | |
| 9,919,068 | B2 | 3/2018 | Shur et al. | |
| 9,974,877 | B2 | 5/2018 | Bettles et al. | |
| 9,981,051 | B2 | 5/2018 | Shur et al. | |
| 9,987,383 | B2 | 6/2018 | Bilenko et al. | |
| 9,999,782 | B2 | 6/2018 | Shur et al. | |
| 10,099,944 | B2 | 10/2018 | Smetona et al. | |
| 2007/0012883 | A1 * | 1/2007 | Lam | C02F 1/325 250/436 |
| 2007/0067930 | A1 * | 3/2007 | Garti | E04H 4/1654 15/1.7 |
| 2008/0316732 | A1 * | 12/2008 | Blake | A01K 63/06 362/101 |
| 2011/0307976 | A1 * | 12/2011 | Ploechinger | A01G 33/00 800/296 |
| 2013/0048545 | A1 | 2/2013 | Shatalov et al. | |
| 2013/0313175 | A1 * | 11/2013 | Weng | A01K 63/045 210/167.22 |
| 2013/0330235 | A1 * | 12/2013 | Stibich | A61L 2/24 422/105 |
| 2014/0074010 | A1 | 3/2014 | Veres et al. | |
| 2014/0166045 | A1 * | 6/2014 | Herring | E04H 4/1654 134/1 |
| 2014/0202962 | A1 | 7/2014 | Bilenko et al. | |
| 2015/0032191 | A1 | 1/2015 | Varghese et al. | |
| 2015/0297767 | A1 | 10/2015 | Gaska et al. | |
| 2015/0336810 | A1 | 11/2015 | Smetona et al. | |
| 2016/0015009 | A1 * | 1/2016 | Prehodka | A01K 63/045 119/259 |
| 2016/0114186 | A1 | 4/2016 | Dobrinsky et al. | |
| 2017/0057842 | A1 | 3/2017 | Dobrinsky et al. | |
| 2017/0100494 | A1 | 4/2017 | Dobrinsky et al. | |
| 2017/0100495 | A1 | 4/2017 | Shur et al. | |
| 2017/0189711 | A1 | 7/2017 | Shur et al. | |
| 2017/0245527 | A1 | 8/2017 | Dobrinsky et al. | |
| 2017/0245616 | A1 | 8/2017 | Lakios et al. | |
| 2017/0248568 | A1 * | 8/2017 | Yizhack | G01N 21/359 |
| 2017/0281812 | A1 | 10/2017 | Dobrinsky et al. | |
| 2017/0290934 | A1 | 10/2017 | Dobrinsky et al. | |
| 2017/0320756 | A1 * | 11/2017 | Trigiani | B06B 1/0215 |
| 2017/0339853 | A1 * | 11/2017 | Sun | A01G 33/00 |
| 2017/0365150 | A1 * | 12/2017 | Bennett | G06F 21/602 |
| 2017/0368215 | A1 | 12/2017 | Shatalov et al. | |
| 2018/0028700 | A1 | 2/2018 | Dobrinsky et al. | |
| 2018/0092308 | A1 | 4/2018 | Barber et al. | |
| 2018/0104368 | A1 | 4/2018 | Dobrinsky et al. | |
| 2018/0117194 | A1 | 5/2018 | Dobrinsky et al. | |
| 2018/0132457 | A1 * | 5/2018 | Bahrebar | A01K 63/045 |
| 2018/0185529 | A1 | 7/2018 | Shur et al. | |
| 2018/0216056 | A1 * | 8/2018 | Mahoney | C12M 21/02 |
| 2018/0221521 | A1 | 8/2018 | Shur et al. | |
| 2018/0243458 | A1 | 8/2018 | Shatalov et al. | |
| 2018/0266131 | A1 * | 9/2018 | Witelson | E04H 4/1209 |
| 2018/0339075 | A1 | 11/2018 | Kennedy et al. | |
| 2019/0030477 | A1 | 1/2019 | Shatalov | |
| 2019/0099613 | A1 | 4/2019 | Estes et al. | |
| 2019/0100718 | A1 | 4/2019 | Estes et al. | |
| 2019/0145901 | A1 * | 5/2019 | Ormeci | G01J 3/42 |

* cited by examiner

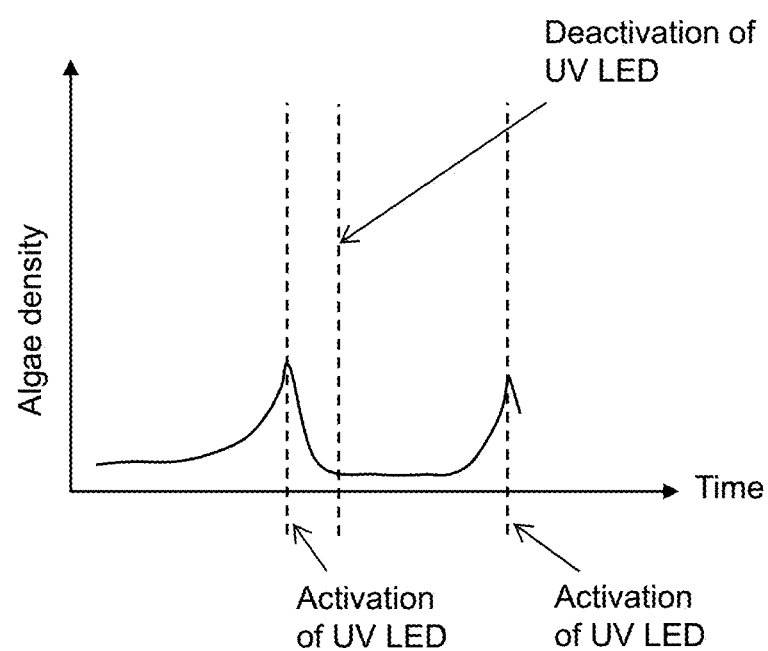
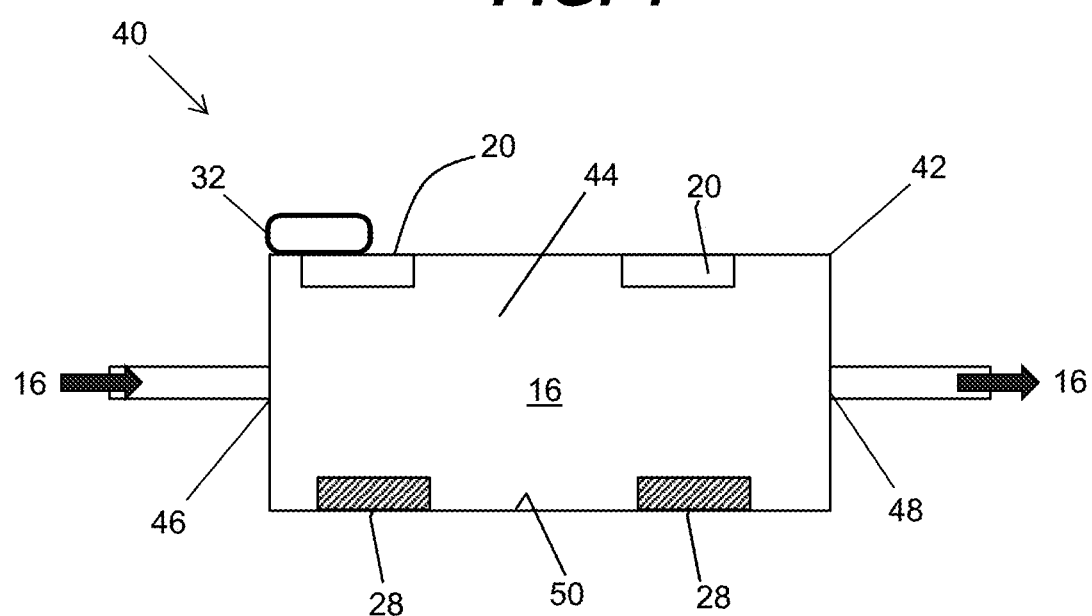

ULTRAVIOLET IRRADIATION OF AQUATIC ENVIRONMENT

REFERENCE TO RELATED APPLICATIONS

The present patent application claims the benefit of U.S. Provisional Application No. 62/566,425, which was filed on 30 Sep. 2017, and is hereby incorporated by reference.

TECHNICAL FIELD

The disclosure relates generally to ultraviolet treatment of fluids, and more specifically, to a solution for using ultraviolet radiation for sterilizing, disinfecting, and/or cleaning fluids and surfaces associated with an aquatic environment.

BACKGROUND ART

An aquarium is one type of aquatic environment that has long been popular both in homes and offices for displaying a wide variation of aquatic life. In general, an aquarium tends to be susceptible to contamination by parasites and other microorganisms which are harmful to the aquatic life, particularly fish. Chemical additives that act as parasiticidal agents are available to address the problems created by the accumulation of harmful contaminants and microorganisms. However, these chemical agents tend to have a disruptive effect on the aquatic environment, often to the detriment of the flora and fauna within the aquarium.

One approach to avoiding the issues associated with using harmful chemical agents entails removing the aquatic life from an aquarium and completely replacing all of the water. This solution is less than satisfactory since many of the contaminants and microorganisms are carried over into the new water supply with the returned aquatic life. The harmful microorganisms again multiply forcing a subsequent water change. In addition, water changes can inflict unnecessary risks upon the aquatic life through changes in pH levels, water temperature and general water chemistry.

Another approach utilizes water treatment systems to treat the water in an aquarium. Typically, these water treatment systems require the attachment of unsightly components in full view on the side of the aquarium. Also, water treatment systems that sterilize water generally treat the water exterior to the aquarium for purposes of avoiding safety hazards associated with the relatively high voltages involved in powering a sterilizer assembly. This requires additional tubing, plumbing or other conduits to draw water from the aquarium into the sterilizer assembly for sterilization, which decreases efficiency. These additional components also increase both manufacturing and maintenance costs with operating an aquarium, as well as necessitate the need for additional space beyond the room required for the aquarium. In addition, leaks or overflow of water are likely to occur due to the external configuration of these components, which can lead to damage of furniture and other objects that are in the vicinity of the aquarium.

SUMMARY OF THE INVENTION

This Summary Of The Invention introduces a selection of certain concepts in a brief form that are further described below in the Detailed Description Of The Invention. It is not intended to exclusively identify key features or essential features of the claimed subject matter set forth in the Claims, nor is it intended as an aid in determining the scope of the claimed subject matter.

Aspects of the present invention are directed to solutions that use ultraviolet radiation for sterilizing, disinfecting, and/or cleaning fluids and surfaces associated with an aquatic environment. In the various embodiments, at least one ultraviolet radiation source such as an ultraviolet light emitting device can be used to irradiate a body of fluid in an aquatic environment as well as the surfaces located about the aquatic environment. An ultraviolet light emitting diode is one example of a type of ultraviolet light emitting device that can be used to irradiate the aquatic environment. Use of one or more ultraviolet light emitting diodes allows a sterilizer for an aquatic environment (e.g., an aquarium) that operates as either a sole unit or a component within a water treatment system to have a significantly simplified design. For example, ultraviolet light emitting diodes offer robust technology which does not utilize high voltages which can be the case with water sterilizers that employ mercury lamps. In addition, ultraviolet light emitting diodes can be easily turned on and off. Also, ultraviolet light emitting diodes do not require quartz enclosures which can be the case with other sources such as mercury lamps. Further, ultraviolet light emitting diodes can operate at any place within an aquatic environment since they can be manufactured as small devices, obviating the need to have the sterilizers operate as an external unit. Having the ultraviolet light emitting diodes operate at any place within an aquatic environment enables a distributed network of ultraviolet light emitting diodes to be configured to operate over various parts of the aquatic environment. In this manner, the distributed network of the ultraviolet light emitting diodes can be wirelessly connected or in a wired connection, and can communicate with a control unit.

The ultraviolet light emitting diodes, like any of the ultraviolet radiation sources of the various embodiments, can be configured to operate at peak wavelengths that facilitate sterilization, disinfection and general cleaning of the fluid in the aquatic environment, as well as any of the surfaces associated with the environment, that remove harmful contaminants, bacteria, parasites, micro-organisms and the like, such as for example, algae. In one embodiment, the ultraviolet radiation sources can be configured to operate at a set of peak wavelengths that remove algae and suppress further growth of the algae. For example, the ultraviolet radiation sources can be configured to operate at a set of peak wavelengths ranging from 250 nm to 280 nm. In one embodiment, the ultraviolet radiation sources can be configured to operate at a peak wavelength of 275 nm.

In the various embodiments, at least one sensor can detect conditions of the aquatic environment including fluid conditions and/or surface conditions associated with the aquatic environment. A number of different sensors can be used singly or in a multiple combinations to detect fluid conditions and/or surface conditions of the aquatic environment. The sensors can include, but are not limited to, a fluid transparency sensor to detect the transparency of a fluid, an ultraviolet radiation sensor to detect the ultraviolet intensity of the fluid, a fluorescent sensor to detect the fluorescence emissivity of the fluid after irradiation by one or more ultraviolet radiation source, and a chemical sensor to detect chemical components in the fluid.

In one embodiment, an ultraviolet radiation sensor can be configured to detect the ultraviolet intensity of the fluid in the aquatic environment after being irradiated with ultraviolet radiation, while a fluorescent sensor can be configured to detect the fluorescent illumination intensity of the fluid after being irradiated by another ultraviolet radiation source. In this manner, a control unit can receive signals indicative of the conditions detected by the ultraviolet radiation sensor and the fluorescent sensor, and determine a fluid transparency of the fluid and an algae density level. If the control unit determines that the algae density level is too high (e.g., the algae density level satisfies a predetermined threshold), then it can activate the operation of the ultraviolet radiation source(s) to eradicate the algae. In addition, the control unit and the sensors can be configured to manage the irradiation of the fluid by monitoring conditions of the fluid during irradiation and adjusting the irradiation parameters of the ultraviolet radiation source(s) as a function of the detected ultraviolet intensity in the fluid and the detected fluorescent illumination intensity.

In one embodiment, a chemical sensor can be used to detect chemical components within the fluid, while a control unit can be used to determine a pH balance and a chlorine level in the fluid as a function of the detected chemical components. To this extent, the control unit can be configured to activate the operation of the ultraviolet radiation source(s) if the pH balance and the chlorine level in the fluid satisfies a predetermined threshold. The control unit and the chemical sensor can then operate in conjunction to monitor the irradiation of the fluid by the source(s). For example, the control unit can adjust the irradiation parameters of the ultraviolet radiation source(s) as a function of the determined pH balance and the chlorine level in the fluid.

In one embodiment, a visible camera can be used to obtain images from various locations about the aquatic environment. In this manner, a control unit can be configured to compares images from each of the locations obtained by the visible camera over different times to determine the presence of algae growth. As a result, the control unit can direct the ultraviolet radiation source(s) to irradiate any location about the aquatic environment determined to have a presence of algae growth.

The operation of the at least one ultraviolet radiation source and sensor with the control unit enables the various embodiments to incorporate a feedback mechanism that facilitates monitoring the quality of the fluid within the aquatic environment. For example, this feedback mechanism enables the control unit to determine a presence of algae growth or other harmful contaminants about the aquatic environment based on the conditions detected by the sensor(s). This allows the control unit to direct the ultraviolet radiation source(s) to irradiate the aquatic environment at locations where there is a presence of algae growth or other harmful contaminants for removal and suppression thereof. In addition, the control unit can monitor the irradiation of the aquatic environment with feedback from the conditions detected by the sensor(s). As a result, the control unit can adjust the irradiation parameters of the ultraviolet radiation source(s) as a function of conditions detected by the sensor(s). The irradiation parameters can comprise the wavelength of the ultraviolet radiation emitted by the ultraviolet radiation source(s), an intensity or overall dosage of the ultraviolet radiation delivered to a volume or body of the fluid by the ultraviolet radiation source(s), and a treatment time that the ultraviolet radiation source(s) deliver the ultraviolet radiation to the fluid. Other irradiation parameters can include, but are not limited to, a power setting for operating the ultraviolet radiation source(s), and a maximum operating temperature of the ultraviolet radiation source(s).

The control unit can include a number of different components that enable it to control the ultraviolet radiation source(s) and make any determinations relating to the quality of the fluid within the aquatic environment based on data obtained from the sensor(s). For example, other components that may be utilized with the control unit can include a timer, an input component, an output component and a power supply. The timer can be set in accordance with the specified treatment time in order to ensure that the ultraviolet radiation source(s) deliver a sufficient dosage to the fluid and/or surfaces of the aquatic environment. The input component can permit a user to adjust at least one of the above-noted irradiation parameters, and the output component can indicate status information of the treatment of the fluid and/or surfaces in the aquatic environment (e.g., on, off, treated, needs treatment, etc.), as well as generate information of more specific details of the treatment. The power supply can provide power to all of these components. These components are not limited to use with only the control unit, but can also be implemented as parts of an irradiation system and used to operate in conjunction with the control unit, ultraviolet radiation source(s) and the sensor(s).

The ultraviolet radiation source(s) and the sensor(s) can be integrated in a housing, a chamber, an enclosure, or the like, and arranged in a variety of locations about the body of fluid and/or surfaces associated with the aquatic environment to remove and suppress the growth of harmful contaminants, bacteria, parasites, micro-organisms and the like, such as for example, algae. In one embodiment, the housing can be immersible within the body of fluid of the aquatic environment. For example, the housing can include a chamber that is immersible in the fluid, an inlet for permitting passage of fluid into the chamber, and an outlet for permitting passage of the fluid out from the chamber. The ultraviolet radiation source(s) and the sensor(s) can be disposed about the chamber in a number of locations that include, but are not limited to, on an internal wall of the chamber, on an external wall of the chamber, or suspended within the chamber. In order to facilitate the irradiation of the fluid, the chamber can have an internal wall surface with an ultraviolet reflective material that extends between the inlet and the outlet to recycle the radiation.

In one embodiment, the housing can be configured for placement on a portion of a walled surface of the aquatic environment. For example, the housing can be arranged such that at least one ultraviolet radiation source irradiates an inner portion of the walled surface. In an embodiment, the inner portion of the walled surface can include a photocatalyst material that undergoes a photocatalytic reaction in response to being irradiated by ultraviolet radiation. This photocatalytic reaction can facilitate the removal and suppression of algae growth or other contaminants from the inner portion of the walled surface of the aquatic environment.

In one embodiment, the housing can be magnetically coupled to a portion of the walled surface of the aquatic environment. For example, the housing can include a first magnetic housing section and a second magnetic housing section magnetically coupled to the first magnet housing section. The first magnetic housing section can be separated from the second magnetic housing section by the walled surface. In one embodiment, at least one sensor can be located in the first magnetic housing section and at least one ultraviolet radiation source can be located in at least one of the first magnetic housing section and the second magnetic housing section. The second magnetic housing section can have a magnetic guide component that is moveable over an outer portion of the walled surface. To this extent, movement of the magnetic guide component in a direction over the outer portion of the walled surface will facilitate movement of the first magnetic housing section along the inner portion of the walled surface in a corresponding direction. In this configuration, the ultraviolet radiation source(s) can direct ultraviolet radiation towards the inner portion of the walled surface to remove algae and suppress further algae growth and/or direct ultraviolet radiation toward the body of fluid for treatment thereof that can include disinfection and sterilization. In one embodiment, the control unit can be configured to activate operation of the ultraviolet radiation source(s) in response to a sensor detecting movement of the first magnet housing section and the second magnet housing section.

In any of various embodiments described herein, a fluid permeable, ultraviolet radiation blocking material can be placed in the aquatic environment in a portion of the body of fluid. The fluid permeable, ultraviolet radiation blocking material can separate the portion of the body of fluid into a first section containing only fluid and a second section containing fluid and biota. In one embodiment, at least one ultraviolet radiation source can be configured to irradiate the fluid in the first section for removal of any algae growth or other contaminants. In operation, the fluid permeable, ultraviolet radiation blocking material prevents the irradiation of the fluid and biota in the second section, while permitting the algae or other contaminants removed from the first section to pass through and collect at a bottom portion of the second section of the aquatic environment. In one embodiment, the fluid permeable, ultraviolet radiation blocking material can include a top surface facing the first section and a bottom surface facing the second section. In an embodiment, the top surface can have an ultraviolet reflective material configured to recycle ultraviolet radiation within the first section. A plurality of spaced channels can extend irregularly from the top surface to the bottom surface to permit a flow of fluid between the first section and the second section. A plurality of spaced voids can be formed in an internal portion between the top surface and the bottom surface. In one embodiment, each void can be formed between a pair of adjacent channels extending between the top surface and the bottom surface.

The various embodiments can be further configured with other components that complement the irradiation of the aquatic environment in order to further enhance the sterilization, disinfection, treatment, and the like, of the fluid and surfaces of the aquatic environment. For example, a filtering unit having a filter element can be configured in the aquatic environment to filter the fluid. In one embodiment, at least one ultraviolet radiation source can be integrated within the filtering unit to irradiate the filter element. In one embodiment, the control unit can direct the ultraviolet radiation source integrated within the filter unit to irradiate the filter element in response to detecting conditions within the aquatic environment that are indicative of contamination in the fluid. Other components that can enhance the sterilization, disinfection, treatment, and the like, of the fluid and surfaces of the aquatic environment include utilizing a visible light emitting source to irradiate the aquatic environment with visible light. To this extent, the visible light emitting source can aid the ultraviolet radiation source(s) in removing algae or other contaminants and suppressing further growth.

A first aspect of the invention provides an ultraviolet illuminator for treating an aquatic environment having a body of fluid interacting with biota, comprising: at least one ultraviolet radiation source configured to irradiate the aquatic environment; at least one sensor to detect conditions of the aquatic environment including fluid conditions and/or surface conditions associated with the aquatic environment; and a control unit, operatively coupled to the at least one ultraviolet radiation source and the at least one sensor, wherein the control unit is configured to determine a presence of algae growth about the aquatic environment, direct the at least one ultraviolet radiation source to irradiate aquatic environment at locations where there is a presence of algae growth for removal thereof and suppression of further algae growth, monitor the irradiation of the aquatic environment with the at least one sensor, and adjust irradiation parameters of the at least one ultraviolet radiation source as a function of conditions detected by the at least one sensor.

A second aspect of the invention provides a system, comprising: an aquatic environment having a body of fluid interacting with biota and a walled surface that defines an area encompassing the body of fluid and the biota; and an ultraviolet illuminator for treating the aquatic environment, the ultraviolet illuminator comprising: a housing configured for placement in a plurality of locations about the aquatic environment; a set of ultraviolet radiation sources located about the housing to irradiate the aquatic environment; a set of sensors to detect conditions of the aquatic environment including fluid conditions and/or surface conditions associated with the aquatic environment; and a control unit, operatively coupled to the set of ultraviolet radiation sources and the set of sensors, wherein the control unit is configured to determine a presence of algae growth about the aquatic environment, direct the set of ultraviolet radiation sources to irradiate aquatic environment at locations where there is a presence of algae growth for removal thereof and suppression of further growth, monitor the irradiation of the aquatic environment with the set of sensors, and adjust irradiation parameters of the set of ultraviolet radiation sources as a function of conditions detected by the set of sensors.

A third aspect of the invention provides a system, comprising: an aquatic environment having a body of fluid interacting with biota and a walled surface that defines an area encompassing the body of fluid and the biota; an ultraviolet illuminator for treating the aquatic environment, the ultraviolet illuminator comprising: a housing configured for placement in a plurality of locations about the aquatic environment; a set of ultraviolet radiation sources located about the housing to irradiate the aquatic environment; a set of sensors to detect conditions of the aquatic environment including fluid conditions and/or surface conditions associated with the aquatic environment, wherein at least one of the plurality of sensors comprises a visible camera configured to obtain images from various locations about the aquatic environment; and a control unit, operatively coupled to the set of ultraviolet radiation sources and the set of sensors, wherein the control unit is configured to determine a presence of algae growth about the aquatic environment by comparing images from each of the locations obtained by the visible camera over different times, direct the set of ultraviolet radiation sources to irradiate aquatic environment at locations where there is a presence of algae growth for removal thereof and suppression of further growth, monitor the irradiation of the aquatic environment with the visible camera, and adjust irradiation parameters of the set of ultraviolet radiation sources as a function of conditions detected by the visible camera; and a fluid permeable, ultraviolet radiation blocking material configured for placement in the aquatic environment in a portion of the body of fluid, the fluid permeable, ultraviolet radiation blocking material separating the portion of the body of fluid into a first section containing only fluid and a second section containing fluid and biota, wherein the plurality of ultraviolet radiation sources are configured to irradiate the fluid in the first section for removal of the algae growth, while the fluid permeable, ultraviolet radiation blocking material prevents the irradiation of the fluid and biota in the second section, and permits the algae removed from the first section to pass through and collect at a bottom portion of the second section.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 3 shows an example of a time dependent graphical representation depicting the removal or sterilization of algae from an aquatic environment with the application of ultraviolet radiation generated from an ultraviolet radiation source according to an embodiment.

FIG. 4 shows a schematic of an ultraviolet illuminator having at least one ultraviolet radiation source, at least one sensor and a control unit according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
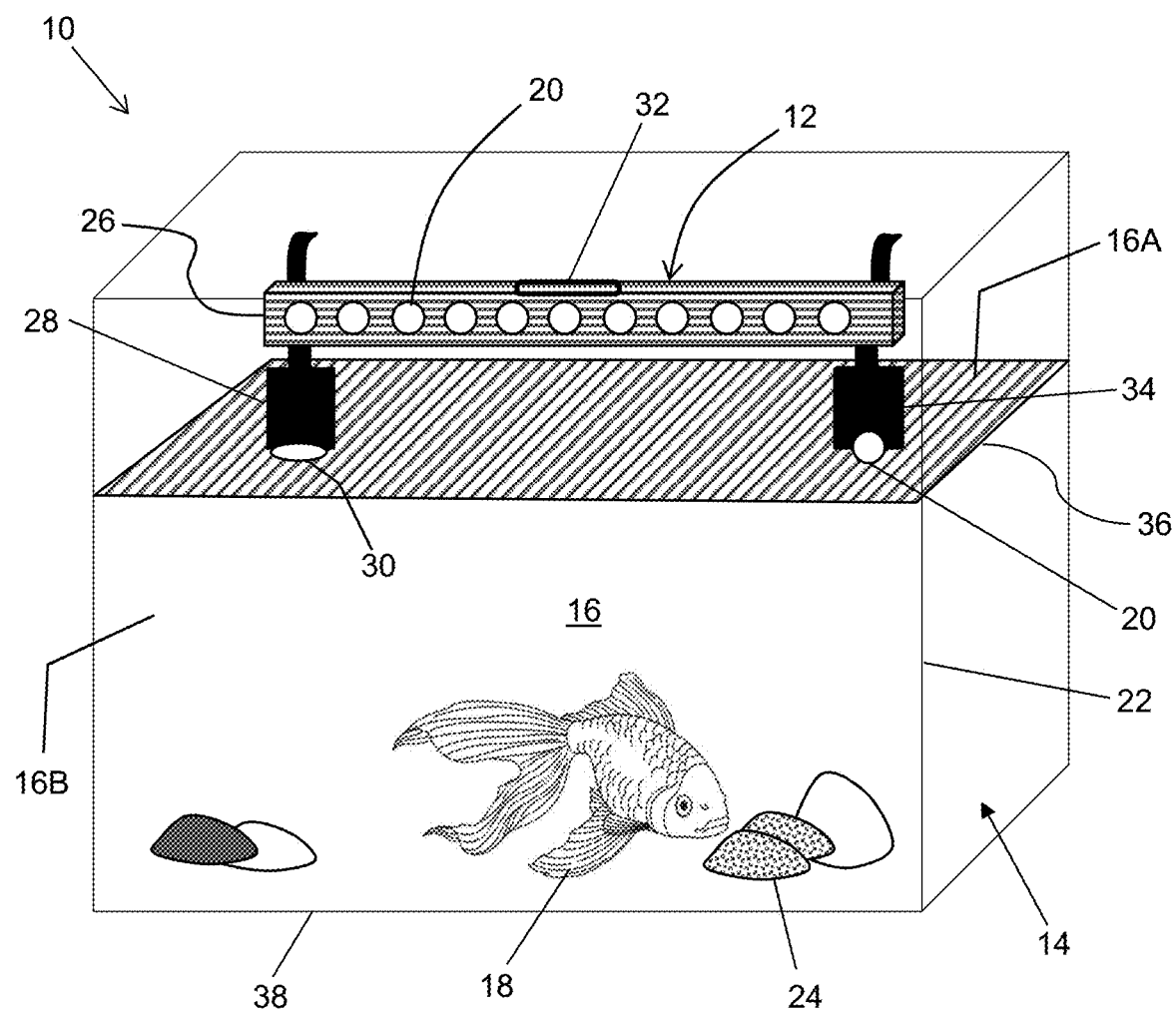
FIG. 1 shows a schematic of a system including an ultraviolet illuminator for irradiating an aquatic environment with ultraviolet radiation according to an embodiment.

As indicated above, aspects of the invention are directed to systems for irradiating an aquatic environment for purposes of sterilizing, disinfecting, and/or cleaning fluids and surfaces associated with the aquatic environment. Although the various embodiments are described with respect to an aquarium, it is understood that the teachings of these embodiments are suited for use with any other type of aquatic environment that may have a need for removal of microorganisms, parasitic agents, bacteria, viruses, germs or other contaminants. Examples of other aquatic environments which the various embodiments are suitable for use with include, but are not limited to, pools, lakes, streams, rivers, and the like. In addition, for the most part, the various embodiments are described with respect to removing or eliminating algae and suppressing further growth of algae in an aquarium, however, it is understood that the embodiments can be directed to removing and suppressing the growth of other aquatic organisms and/or contaminants in an aquatic environment. Examples of other aquatic organisms and contaminants that the embodiments can be directed to include, but are not limited to, pond scum, algal bloom, any other aquatic organism that can conduct photosynthesis that can be undesirable and/or harmful to the body of fluid and biota present in the aquatic environment, as well as the surrounding areas and surfaces that encompass the aquatic environment.

As used herein, ultraviolet irradiation of a body or volume of fluid, and/or the surfaces of an aquatic environment, can entail sanitizing, disinfecting, and/or sterilizing. Sanitizing generally means reducing the number of bacterial contaminants to a predetermined safe level. Disinfecting generally means destroying pathogenic and other types of microorganisms, while sterilizing can be more extensive in that it kills all microbial forms and/or include destroying the ability of the microbial forms to reproduce.

Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

Generally, ultraviolet radiation, and in particular, UV-B radiation and UV-C radiation is "germicidal," i.e., it deactivates the DNA of bacteria, viruses and other pathogens, and thus, destroys their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. Ultraviolet radiation with a wavelength of approximately between about 250 nm to about 290 nm provides the highest germicidal effectiveness, while an ultraviolet radiation between about 260 nm to about 310 nm is sufficient for providing overall germicidal effectiveness, and ultraviolet radiation between 250 nm to 280 nm is a range for facilitating sterilization and disinfection of an aquatic environment that can eliminate and suppress algae growth suppression, with 275 nm being a preferable peak wavelength. While susceptibility to ultraviolet radiation varies, exposure to ultraviolet energy in the above range for about 20 to about 34 milliwatt-seconds/cm$^2$ is adequate to deactivate approximately 99 percent of the pathogens.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through. Also, unless otherwise noted, the term "set" means one or more (i.e., at least one) and the phrase "any solution" means any now known or later developed solution.

The aquatic environment irradiation systems including ultraviolet illuminators described herein can include a number of components described below in more detail, some of which may be optional, that facilitate the treatment of fluids and surfaces associated with an aquatic environment. The modalities used with the various aquatic environment irradiation systems described herein including its respective components can include any now known or later developed approaches that incorporate the concepts of the embodiments described below in more detail.

The description that follows may use other terminology herein for the purpose of only describing particular embodiments and is not intended to be limiting of the disclosure. For example, unless otherwise noted, the term "set" means one or more (i.e., at least one) and the phrase "any solution" means any now known or later developed solution. The singular forms "a," "an," and "the" include the plural forms as well, unless the context clearly indicates otherwise. It is further understood that the terms "comprises," "comprising," "includes," "including," "has," "have," and "having" when used in this specification, specify the presence of stated features, integers, steps, operations, elements, and/or components, but do not preclude the presence or addition of one or more other features, integers, steps, operations, elements, components, and/or groups thereof.

Turning to the drawings, FIG. 1 shows a schematic of a system 10 including an ultraviolet illuminator 12 for irradiating an aquatic environment 14 with ultraviolet radiation according to an embodiment. As shown in FIG. 1, the aquatic environment 14 can include an aquarium having a volume or body of fluid 16 such as water interacting with biota 18 that can include, but is not limited to marine life and plant life. In addition, the aquarium can include other objects that the biota can interact with and/or serve as decorations or ornaments such as rocks (e.g., fluorescent rocks), sunken chests, boats, and the like.

The ultraviolet illuminator 12 can include at least one ultraviolet radiation 20 source configured to irradiate the aquatic environment 14. In one embodiment, as shown in FIG. 1, the ultraviolet illuminator 12 can include a set of ultraviolet radiation sources 20 each configured to emit ultraviolet radiation in the aquatic environment 14 to effectuate an ultraviolet treatment of the fluid 16 and walled surfaces 22 as well as any surfaces of ornamental or decorative objects 24 (e.g., decorations and ornaments) in the aquarium. This ultraviolet treatment can include sterilizing at least one of the fluid 16, the walled surfaces 22, or the ornamental objects 24 for removing or eliminating algae or contaminants and suppressing further growth. In addition, the ultraviolet treatment by the set of ultraviolet radiation sources 20 can include sterilizing and/or disinfecting the fluid 16.

The set of ultraviolet radiation sources 20 can be placed in one of a plurality of locations about the aquatic environment. As used herein, "about the aquatic environment" means immersed in the body of fluid, suspended above the fluid, against an inner wall surface or against an outer wall surface of the aquatic environment. It is understood that in any of these locations, the ultraviolet radiation sources 20 can be oriented to direct ultraviolet radiation in a manner as desired to effectuate the ultraviolet treatment of the fluid 16, the walled surfaces 22, and/or the ornamental objects 24. For example, the ultraviolet radiation sources 20 can be configured with moveable degrees of freedom to facilitate irradiation of desired locations about the aquatic environment 14.

The set of ultraviolet radiation sources 20 can comprise any combination of one or more ultraviolet radiation emitter. For example, the set of ultraviolet radiation sources 20 can include a high intensity ultraviolet lamp (e.g., a high intensity mercury lamp), a discharge lamp, ultraviolet light emitting diodes (LEDs), super luminescent LEDs, laser diodes, and/or the like. In an embodiment, the set of ultraviolet radiation sources includes a set of light emitting diodes manufactured with one or more layers of materials selected from the group-III nitride material system (e.g., $Al_xIn_yGa_{1-x-y}N$, where $0 \leq x$, $y \leq 1$, and $x+y \leq 1$ and/or alloys thereof). Additionally, the set of ultraviolet radiation sources 20 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a wave guide, a plurality of ultraviolet fibers, each of which terminates at an opening, a diffuser, and/or the like. In addition, optical elements including but not limited to, lenses, prismatic ultraviolet transparent elements, mirror elements (e.g., a parabolic mirror element, an omnidirectional mirror, a planar mirror and/or the like) can be deployed for focusing the radiation in a particular pattern and/or direction.

Figure 2A:
FIGS. 2A-2B show views of a housing for an ultraviolet illuminator containing a set of ultraviolet radiation sources, such as ultraviolet light emitting devices, configured for placement about an aquatic environment according to an embodiment.
Figure 2B:
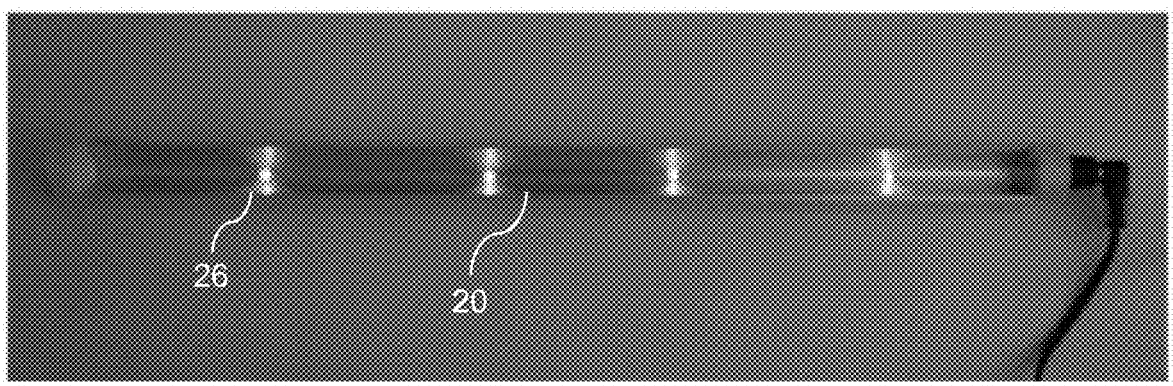

In one embodiment, the set of ultraviolet radiation sources 20 can be enclosed within a housing 26. As an example, FIGS. 2A-2B show views of a housing 26 with a set of ultraviolet radiation sources 20 in the form of an ultraviolet light emitting device sterilizing module in an off-state (FIG. 2A) and in an on-state (FIG. 2B). In this example, the ultraviolet light emitting device sterilizing module of FIGS. 2A-2B are tubes enclosing a set of ultraviolet light emitting devices such as for example, UV LEDs.

Referring back to the example illustrated in FIG. 1, the housing 26 with the set ultraviolet radiation sources 20 can be positioned above the fluid 16 (e.g., suspended by fastener assembly). It is understood that the housing 26 with the set of ultraviolet radiation sources 20 can be positioned in other locations about the aquatic environment 14. For example, the housing 26 can be positioned in the fluid 16 (e.g., immersed) and/or against any of the walled surfaces 22. Further, it is understood that the number of ultraviolet radiation sources 20 that can be utilized within the housing 26 can vary as desired.

In one embodiment, the housing 26 can include an ultraviolet transparent fluoropolymer that encapsulates the set of ultraviolet radiation sources 20 contained therein, as well as any other sources and sensors that maybe integrated in the housing. In this manner, the ultraviolet transparent fluoropolymer can isolate the ultraviolet radiation sources 20 from the fluid 16, the biota 18 and the ornamental objects 24. Ultraviolet transparent polymers that include, but are not limited to, fluorinated ethylene propylene (FEP), tetrafluoroethylene hexafluoropropylene vinylidene fluoride (THV), polytetrafluoroethylene (PTFE), and/or the like, are examples of ultraviolet transparent material that are suitable for use as a housing in these embodiments as well as others described herein. It is understood that the housing can include other ultraviolet transparent materials that are chemically inert to any interaction with the fluid 16 and chemically stable to withstand exposure to the ultraviolet radiation generated from the ultraviolet radiation sources 20.

The ultraviolet illuminator 12 can also include at least one sensor 28 to detect conditions of the aquatic environment 14 including fluid conditions and/or surface conditions associated with the aquatic environment. In one embodiment, as depicted in FIG. 1, the sensor 28 can include a visible camera 30 configured to obtain images from any of a number of various locations about the aquatic environment 14. For example, the visible camera 30 can be used to detect algae growth in the fluid 16, the biota 18, the ornamental objects 24, or the walled surfaces 22. In one embodiment, the visible camera 30 can have rotational degrees of freedom to facilitate monitoring algae growth throughout the aquatic environment 14. For example, the visible camera 30 can be directed towards any of the walled surfaces 22 of the aquatic environment 14. The monitoring performed by the visible camera 30 can include obtaining views of the aquatic environment 14 including in the fluid 16, on the biota 18, on the ornamental objects 24, or against the walled surfaces 22, at different times to detect the presence of algae due to changes in the aquatic environment. Although the system 10 depicted in FIG. 1 only shows the use of one visible camera 30 it is understood that more cameras can be configured. Also, it is understood that other visible cameras can be located independent of the housing 26 and the ultraviolet radiation sources 20.

In one embodiment, a control unit 32 can be operative coupled to the set of ultraviolet radiation sources 20 and the visible camera 30 to aid in the monitoring of the aquatic environment 14 for algae growth. In particular, the control unit 32 can compare the images from each of the locations in the aquatic environment 14 obtained by the visible camera 30 over different times to determine the presence of algae growth. To this extent, the control unit 32 can direct the set of ultraviolet radiation sources 20 to irradiate any location about the aquatic environment 14 determined to have a presence of algae growth.

The control unit 32 can be implemented to perform similar functions relating to determining the presence of algae growth in the aquatic environment 14 in embodiments that use other types of sensors in place of the visible camera 30, or in combination with visible camera to provide feedback on the conditions present in the aquatic environment. For example, the control unit 32 can direct the set of ultraviolet radiation sources 20 to irradiate the aquatic environment 14 at locations where there is a presence of algae growth for removal and suppression of further growth. In addition, the control unit 32 can monitor the irradiation of the aquatic environment with aquatic environment condition data obtained from at least one sensor 28. In this manner, the control unit 32 can adjust one or more irradiation parameters of any of the ultraviolet radiation sources 20 as a function of the conditions detected by the sensor(s) 28. The irradiation parameters can comprise the wavelength of the ultraviolet radiation emitted by the ultraviolet radiation sources, an intensity or overall dosage of the ultraviolet radiation delivered to a volume or body of the fluid by the ultraviolet radiation sources, and a treatment time that the ultraviolet radiation sources deliver the ultraviolet radiation to the fluid and/or surfaces of the aquatic environment. Other irradiation parameters can include, but are not limited to, a power setting for operating the ultraviolet radiation source(s), and a maximum operating temperature of the ultraviolet radiation sources. It is understood that the control unit 32 can perform similar actions for other control operations such as monitoring the level of contaminants within the fluid 16.

In one embodiment, the control unit 32 can activate the operation of at least one ultraviolet radiation source 20 in response to determining that the presence of an amount of algae, bacteria, germs, viruses, and/or the like, within the fluid 16, on the biota 18, against the walled surfaces 22, or on the ornamental objects 24, exceeds a predetermined threshold, and thus, necessitating an ultraviolet treatment. Activating the operation of the ultraviolet radiation sources 20 by the control unit 32 can include specifying any of the aforementioned irradiation parameters. It is understood that other irradiation parameters can be specified and/or adjusted. Other irradiation parameters can include, but are not limited to, the angular distribution of the ultraviolet radiation transmitted from the ultraviolet radiation sources 20. It is understood that all of these irradiation parameters are illustrative of some of the parameters that can be set by the control unit and are not meant to be limiting as other parameters exist which may be specified.

A timer with switches and/or the like, which can be integrated with the control unit 32 or as a separate component, can be used to manage the duration that the ultraviolet radiation sources 20 are on for a particular ultraviolet treatment and ensure that radiation is applied to the aquatic environment 14 for that duration. In one embodiment, the control unit 32 operating in conjunction with the timer can manage the amount of time that the ultraviolet radiation sources 20 radiate in the UV-C range versus the UV-B range. The duration and frequency that the ultraviolet radiation sources 20 are utilized can depend on detected condition signals provided to the control unit 32 by any of the sensors 28 that are used to monitor the aquatic environment.

In an embodiment, the control unit 32 can include an input component and an output component that allows a user to interact with the system 10 and the ultraviolet illuminator 12. For example, the input component can permit the user to adjust at least one of the aforementioned irradiation parameters. This can include making adjustments during the ultraviolet irradiation treatment and/or prior to initiating a treatment. For example, a user can use the input component to adjust both the intensity and dosage of the ultraviolet radiation generated from the ultraviolet radiation sources 20. In one embodiment, the input component can include a set of buttons and/or a touch screen to enable the user to specify various input selections regarding the irradiation parameters. The output component can include a number of different output devices to present information to the user such as, for example, a vibration device, a visible light (e.g., flashing), an auditory signal generated by a speaker, and/or the like. For example, the output component can include a visual display for providing status information on the ultraviolet irradiation of the aquatic environment 14 (e.g., time remaining, the presence of bacteria, viruses, germs, or the like), the condition of the fluid (e.g., fluid appearance changes, presence of algae), an indication that a ultraviolet irradiation treatment is recommended, an indication that the fluid has been sterilized, disinfected, sanitized, a simple visual indicator that displays whether a ultraviolet treatment is underway (e.g., an illuminated light). or if the treatment is over (e.g., absence of an illuminated light).

In addition to a visible camera 30, a number of different sensors 28 can be used in conjunction with the control unit 32 to detect conditions in the aquatic environment 14 that are indicative of algae growth, and/or other contaminants, micro-organisms, parasitic agents, etc., that can be eradicated and suppressed with the ultraviolet radiation sources 20 and any other types of radiation sources (e.g., visible light emitting sources, infrared sources). One type of sensor that can be deployed can include a fluid transparency sensor that can detect the transparency of the fluid 16. For example, a fluid transparency sensor can emit light through a portion of the fluid toward a light sensor. Based variations in the quantity of light sensed by the sensor, the transparency of the fluid can be determined. A fluorescence sensor, such as a fluorometer, that can detect the fluorescence emissivity of the fluid after irradiation is another type of sensor that can be utilized. Another type of sensor that can be deployed in the irradiation system according to one of the embodiments described herein can include a chemical sensor to detect chemical components of the fluid. Examples of a chemical sensor can include, but are not limited to, a pH sensor, a chlorine sensor, an alkalinity sensor, a nitrate sensor, a salinity sensor, etc.

A bacterial fluorescence sensor is another type of sensor that can be deployed to detect the amount or presence of algae, bacteria, germs, viruses, and/or the like, which is present in the fluid on against the walled surfaces 22. In particular, the bacterial fluorescence sensor can generate signals representative of the condition of the fluid and/or the walled surfaces with respect to the amount of bacteria, germs, viruses, and the like, and send these signals to the control unit 32. In this manner, the control unit 32 can determine whether an ultraviolet treatment is necessary as a function of the signals provided by the bacterial fluorescence sensor using any solution. Additionally, the control unit can determine the progress of the treatment depending on the presence of these signals.

Some of the aforementioned sensors and their operations in conjunction with the control unit 32 are explained below in more detail with respect to other embodiments. It is also understood that the systems of the various embodiments are not meant to be limited to the aforementioned sensors. A multitude of different types of sensors can be used with any of the various embodiments of the present invention. Other sensors that are suitable for use with any of the various embodiments can include, but are not limited to, a temperature sensor, a pressure sensor, and a humidity sensor. Each of these sensors could detect the level or amount of a particular process parameter that each is intended to measure and send signals thereof to the control unit 32. For example, a temperature sensor can detect the temperature of the fluid 16 and/or the temperature of any of the walled surfaces 22 of the aquatic environment 14. These sensors can be deployed along with the ultraviolet radiation sources 20 in any desired configuration. For example, the sensors can be interspersed in the housing 26 with the ultraviolet radiation sources 20 or separated from the housing.

Both the control unit 32 and the sensor(s) 28 can include a wireless transmitter and receiver that is configured to facilitate communications with each other at a remote location via WiFi, BLUETOOTH, and/or the like. As used herein, a remote location is a location that is apart from any of the irradiation systems described herein. For example, a remote computer can be used to transmit operational instructions to the wireless transmitter and receiver. The operational instructions can be used to program functions performed and managed by the control unit 32 and the sensors 28. In another embodiment, the wireless transmitter and receiver can transmit ultraviolet treatment results, data from and to the remote computer, to facilitate maintenance and diagnostic operations on the irradiation systems.

The irradiation system 10 of FIG. 1 as well as the systems of the other embodiments described herein can further include a power source that is configured to power each of the ultraviolet radiation sources 20, the control unit 32 and the sensors 28. In one embodiment, the power source can take the form of one or more batteries, a vibration power generator that can generate power based on magnetic inducted oscillations or stresses developed on a piezoelectric crystal. In another embodiment, the power source can include a super capacitor that is rechargeable. Other power components that are suitable for use as the power source for the irradiation system 10, the control unit 32 and the sensors 28 can include a mechanical energy to electrical energy converter such as a piezoelectric crystal, and a rechargeable device.

The irradiation systems of the various embodiments can also include a heat dissipating component. A heat dissipating component enables the electronic componentry associated with the ultraviolet radiation sources 20, the control unit 32, the sensors 28 and the power source to operate efficiently without overheating. Examples of a heat dissipating component can include, but are not limited to, a heat sink, an air fan, and/or other heat dissipating mechanisms, such as liquid heating.

FIG. 1 shows the system 10 can utilize other components that facilitate the optimized irradiation of the aquatic environment 14 including the fluid 16, the biota 18, the walled surfaces 22 and the ornamental objects 24. For example, the system 10 can include a filtering unit 34 having a filter element such as a filtering membrane, cartridge, matrix, or the like that is configured to filter the fluid 16 in the aquatic environment 14 to remove a variety of contaminants. The filter element can include filtering material such as for example, AAO, porous silicon oxide, carbon and various phases of carbon, and/or the like. In one embodiment, as depicted in FIG. 1, at least one ultraviolet radiation source 20 can be integrated within the filtering unit 34. In this manner, the ultraviolet radiation source 20 can be used to irradiate the filter element of the filtering unit 34. In one embodiment, the control unit 32 can direct the ultraviolet radiation source 20 to irradiate the filter element in response to detecting conditions that are indicative of contaminants in the fluid 16 (e.g., from conditions detected by the visible camera 30 or other sensors 28). To this extent, the ultraviolet radiation source 20 can be used to direct ultraviolet radiation to the filter element of the filtering unit 34 for algae inactivation of algae that has collected in the filter element, and for sterilization of various bacteria residue stored in the filter element.

A fluid permeable, ultraviolet radiation blocking material 36 configured for placement in the aquatic environment 14 in a portion of the body of fluid 16 is another example of a component that can be used in the system 10 to facilitate the optimized irradiation of the aquatic environment 14. In one embodiment, as shown in FIG. 1, the fluid permeable, ultraviolet radiation blocking material 36 can separate the portion of the body of fluid 16 into a first section 16A containing only fluid and a second section 16B containing fluid, biota and ornamental objects 24. With this configuration, the set of ultraviolet radiation sources 20 can be configured to irradiate the fluid 16 in the first section 16A for removal of the algae growth, while the fluid permeable, ultraviolet radiation blocking material 36 prevents the irradiation of the fluid and biota in the second section 16B. In one embodiment, the fluid permeable, ultraviolet radiation blocking material 36 can permit the algae removed from the first section 16A to pass through and collect at a bottom portion 38 of the aquatic environment 14 in the second section 16B.

The fluid permeable, ultraviolet radiation blocking material 36 can comprise a water permeable mesh that is not transparent to ultraviolet radiation. In one embodiment, the water permeable mesh can comprise a plastic film with twisted channels for water penetration. The water permeable mesh can separate the part of the aquatic environment 14 (e.g., aquarium) that undergoes ultraviolet radiation from the part of the environment that contains the living organisms. To this extent, the water permeable mesh can allow for effective ultraviolet sterilization without affecting the living organisms. Further details of the fluid permeable, ultraviolet radiation blocking material 36 are described below with respect to other embodiments depicted in FIGS. 10A-10B and 11.

FIG. 3 shows an example of a time dependent graphical representation depicting the removal or sterilization of algae from an aquatic environment with the application of ultraviolet radiation generated from an ultraviolet illuminator such as the one depicted in FIG. 1. In this representation, ultraviolet radiation is generated from an ultraviolet illuminator at two separate times. As shown in FIG. 3, the ultraviolet illuminator is activated each time the algae density is detected as increasing in the aquatic environment. For example, the ultraviolet illuminator can be activated when the algae density exceeds a predetermined maximum level, a rate of change of the algae density exceeds a predetermined maximum rate, and/or the like. During the duration that the ultraviolet radiation sources of the ultraviolet illuminator are active, the representation of FIG. 3 shows the algae density level decreasing to a barely noticeable level. To this extent, the ultraviolet illuminator can be deactivated when the algae density reaches or is lower than a predetermined minimum level. With the cooperation between the sensor(s) 28, the ultraviolet radiation source(s) 20, and the control unit 32, the ultraviolet illuminator can suppress the growth of algae before it reaches a level that can be harmful to the aquatic environment including the body of fluid and the biota.

FIG. 4 shows a schematic of an ultraviolet illuminator 40 having at least one ultraviolet radiation source 20, at least one sensor 28 and a control unit 32 according to an embodiment. In this embodiment, the ultraviolet illuminator 40 can be configured for immersion in the body of fluid of the aquatic environment. For example, consider an aquatic environment such as an aquarium shown in FIG. 1. In this scenario, the ultraviolet illuminator 40 can be fastened to a top exterior surface by a hook assembly or the like, and immersed in the fluid 16 in a manner similar to the filtering unit 34. In such an arrangement, as explained below in more detail, the ultraviolet illuminator 40 can operate to irradiate the fluid in the aquatic environment to perform actions that can include, but are not limited, sterilization and/or disinfection of the fluid, as well removal and suppression of harmful contaminants including, but not limited to, algae. In addition to operating as a sole illuminator for an irradiation system, it is possible to utilize the ultraviolet illuminator 40 as a complement to another illuminator. For example, the ultraviolet illuminator 40 can be configured to suspend from the housing 26 in FIG. 1 and be immersed in the body of fluid 16 like the visible camera 28 and the filtering unit 34.

As shown in FIG. 4, the ultraviolet illuminator 40 can include a housing 42 having a chamber 44, an inlet 46 for permitting passage of fluid into the chamber and an outlet 48 for permitting passage of the fluid out from the chamber. A set of ultraviolet radiation sources 20 and a set of sensors 28 can be located about the chamber 44. As used herein, "about the chamber" means positioned on an internal wall or an external wall of the chamber 44, or suspended within the chamber between the internal walls. In the embodiment depicted in FIG. 4, the set of ultraviolet radiation sources 20 and the set of sensors 28 can be located on an internal wall 50 of the chamber 44. It is understood that the number and position of the ultraviolet radiation sources 20 and the sensors 28 illustrated in FIG. 4 are only illustrative and not meant to be limiting.

In one embodiment, the sensors 28 in the chamber 44 of the ultraviolet illuminator 40 can include an ultraviolet radiation sensor and a fluorescent sensor (e.g., a fluorescence meter). For example, the first sensor 28 after the inlet 46 can include the ultraviolet radiation sensor and the second sensor just before the outlet 48 can include the fluorescent sensor. In operation, the ultraviolet radiation sensor can detect the ultraviolet intensity in the fluid 16 in the chamber 44 after entering the inlet 46 and being irradiated by a first ultraviolet radiation source 20 (e.g., the first source downstream of the inlet), and the fluorescent sensor can detect the fluorescent illumination intensity of the fluid in the chamber after being irradiated by a second ultraviolet radiation source (e.g., the second source downstream of the inlet 46) before exiting through the outlet 48.

The control unit 32 can operate in conjunction with the set of ultraviolet radiation sources 20 and the set of sensors 28. In one embodiment, the control unit 32 can determine a fluid transparency of the fluid 16 in the chamber 44 as a function of the detected ultraviolet intensity in the fluid. In particular, as a transparent of the fluid decreases, the amount of ultraviolet radiation detected by the set of sensors 28 also will decrease. In addition, the control unit 32 can determine an algae density level within the fluid as a function of the detected fluorescent illumination intensity. In particular, as the algae density level increases, the amount of fluorescent illumination also will increase. It is understood, that other modalities can be utilized to obtain contamination information of the water such as for example, a fluid transparency sensor (e.g., water transparency meter) and an algae detector.

The control unit 32 can activate operation of the ultraviolet radiation sources 20 in the ultraviolet illuminator 40 if the algae density level satisfies a predetermined threshold. It is understood, that if the ultraviolet illuminator 40 is used as sub-component of a larger illuminator tasked to illuminate a greater area of the aquatic environment (e.g., the ultraviolet illuminator 12 depicted in FIG. 1), then the control unit 32, which can be part of the larger illuminator or a control component for the housing 42, can be configured to activate operation of the applicable ultraviolet radiation sources 20 that provide the desired coverage of the aquatic environment. Regardless of these possible arrangements, the control unit 32 can be configured to manage the irradiation of the fluid by 16 monitoring conditions of the fluid during the irradiation and adjust the irradiation parameters of the ultraviolet radiation sources as a function of the detected ultraviolet intensity in the fluid and the detected fluorescent illumination intensity.

In this example, as the fluid 16 enters the chamber 44 of the housing 42, the first ultraviolet radiation source and the ultraviolet radiation sensor work synchronously, such that the ultraviolet sensor can determine the ultraviolet intensity in the chamber 44 after being irradiated by the first radiation source. To this extent, the control unit 32 can calibrate the ultraviolet intensity readings to obtain the water transparency. The second ultraviolet radiation source 20 can comprise a source of ultraviolet radiation selected to elicit a fluorescence response from the expected contaminations within the aquatic environment (e.g., deliver ultraviolet radiation in a peak wavelength range that results in fluorescence of algae). To this extent, the fluorescent sensor can detect the fluorescent illumination intensity in the fluid after being irradiated by the second ultraviolet radiation source (e.g., collect information about the presence of algae).

In one embodiment, the fluorescent sensor can comprise a sensor of multiple fluorescent wavelengths that can be designed to detect the intensity and the wavelength of fluorescent radiation. Using this data, the control unit 32 can determine a level of contamination (e.g., a presence of algae) within the aquatic environment, and power on the ultraviolet radiation sources. In the example in which the ultraviolet illuminator 40 is used as a sub-component of the illuminator 12 depicted in FIG. 1, the control unit 32 can use the detected fluid transparency and fluorescence conditions to control the rate of filtering performed by the filtering unit 34. For instance, the control unit 32 could increase the rate of filtering if it is determined that the detected fluid transparency and fluorescence conditions are indicative of a presence of algae or an increasing density of algae growth.

Figure 5:
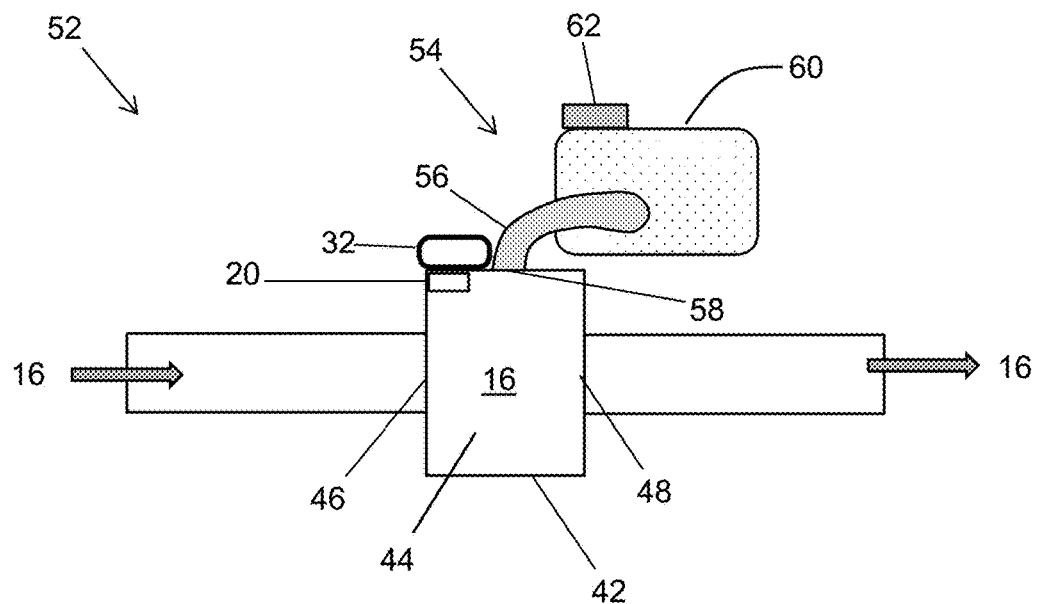
FIG. 5 shows a schematic of an ultraviolet illuminator utilizing a chemical sensor that operates in conjunction with at least one ultraviolet radiation source and a control unit according to an embodiment.

It is understood that this housing arrangement with the chamber 44, the inlet 46 and the outlet 48 can be configured with other sensors and is not meant to be limited to fluid transparency sensing and fluorescent sensing. For example, FIG. 5 shows a schematic of an ultraviolet illuminator 52 utilizing a chemical sensor 54 that operates in conjunction with at least one ultraviolet radiation source 20 and a control unit 32 in a housing 42 having a chamber 44, an inlet 46 and an outlet 48 for detecting chemical components within the fluid 16. As shown in FIG. 5, the chemical sensor 54 can include a conduit 56 (e.g., a channel, a tube, a pipe, a pathway, a cylinder, or the like) fluidly coupled to a port 58 within the chamber 44, a vessel (e.g., a storage container, or the like) 60 for receiving a sample of fluid 16 from the chamber by the conduit, and a chemical component detector 62 to detect the chemical components of the fluid in the vessel.

In one embodiment, the chemical sensor 54 can be used to detect chemical components that relate to the pH balance, the chlorine level, and/or the like, within the fluid 16 which the control unit 32 can be configured to specifically ascertain the pH balance, the chlorine level, and/or the like, in the fluid. In this scenario, the chemical sensor 54 can include a pH sensor, a chlorine sensor, an alkalinity sensor, a nitrate sensor, a salinity sensor, etc. However, it is understood that other chemical sensors can be used to detect other organic chemical compounds that can be found in the body of fluid in an aquatic environment and that can be used in assessing the presence of algae or other contaminants.

In operation, the control unit 32 can be configured to activate operation of the ultraviolet radiation sources 20 in the ultraviolet illuminator 52 if the pH balance and the chlorine level in the fluid 16 satisfies a predetermined threshold. In addition, the control unit 32 can be configured to manage the irradiation of the fluid by monitoring the conditions of the fluid during the irradiation and adjust the irradiation parameters (e.g., the intensity or duration) of the ultraviolet radiation sources as a function of the determined pH balance and the chlorine level in the fluid.

Figure 6:
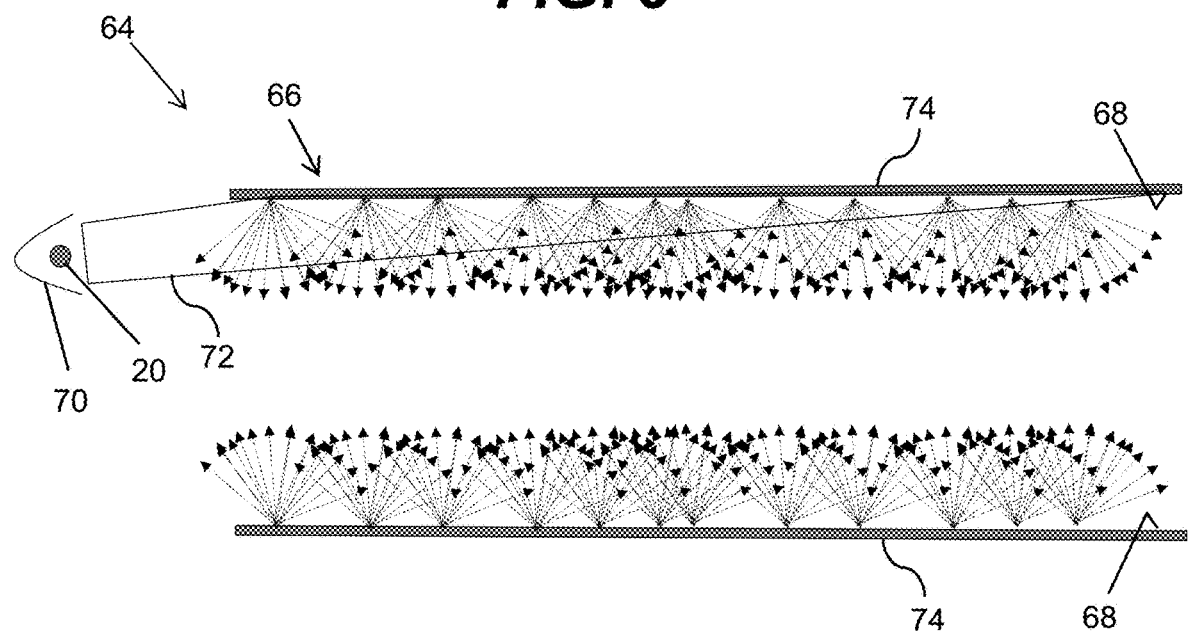
FIG. 6 shows a schematic of a housing for an ultraviolet illuminator that is immersible in an aquatic environment with inner walls having an ultraviolet reflective material according to an embodiment.

In order to recycle or recirculate the ultraviolet radiation emitted from the ultraviolet radiation source(s) in an ultraviolet illuminator, the housing can be configured with ultraviolet reflective material. FIG. 6 shows a schematic of an ultraviolet illuminator 64 with a housing 66 having inner walls 68 with all or at least portion having a layer, film or coating of ultraviolet reflective material. In general, a layer, film or coating of ultraviolet reflective material with a reflection coefficient of at least 50% will enable recycling of the ultraviolet radiation generated from the ultraviolet radiation source(s) 20. As shown in FIG. 6, a parabolic mirror 70 can be positioned about a ultraviolet radiation source 20 to complement the recycling of the ultraviolet radiation 72 within the housing 66 of the ultraviolet illuminator 64 that is provided by the ultraviolet reflective material.

Examples of ultraviolet reflective material that are suitable for use as a layer, film or coating can include, but are not limited to, polished aluminum, Bragg reflective dielectric mirrors, omni-directional mirrors comprising dielectric and metallic layers (e.g., aluminum), and/or the like. In one embodiment, the ultraviolet reflective material can include a diffusive ultraviolet reflective material such as a fluoropolymer. Examples of a fluoropolymer that are suitable as a diffusive ultraviolet reflective material that enables diffusive reflectivity can include, but are not limited to, expanding polytetrafluoroethylene (ePTFE) membrane (e.g., GORE® DRP® Diffuse Reflector Material), polytetrafluoroethylene (PTFE), and/or the like. Other examples of ultraviolet reflective material that can be used to recycle radiation can include, but are not limited to, polished aluminum, Bragg reflective dielectric mirrors, omni-directional mirrors comprising dielectric and metallic layers (e.g., aluminum), and/or the like.

It is understood that the surfaces of the inner wall 68 of the housing 66 of the ultraviolet illuminator 64 can be implemented with one or more of the above-noted modalities that can recycle or recirculate ultraviolet radiation generated from the ultraviolet radiation source 20. For example, the surfaces of the inner wall 68 of the housing 66 can have portions with both ultraviolet reflective material and diffusive ultraviolet reflective material. Those skilled in the art will appreciate that there are a multiple of different combinations that can be used with the inner wall surfaces of the housing 66 to recycle or recirculate ultraviolet radiation.

In one embodiment, the housing 66 of the ultraviolet illuminator 64 can have exterior walls 74 formed of an ultraviolet absorbing material that prevents the release of ultraviolet radiation from the housing. Examples of ultraviolet absorbing material can include, but are not limited to, many types of glass and plastic, as well as most metals without a heavily polished surface.

Figure 7:
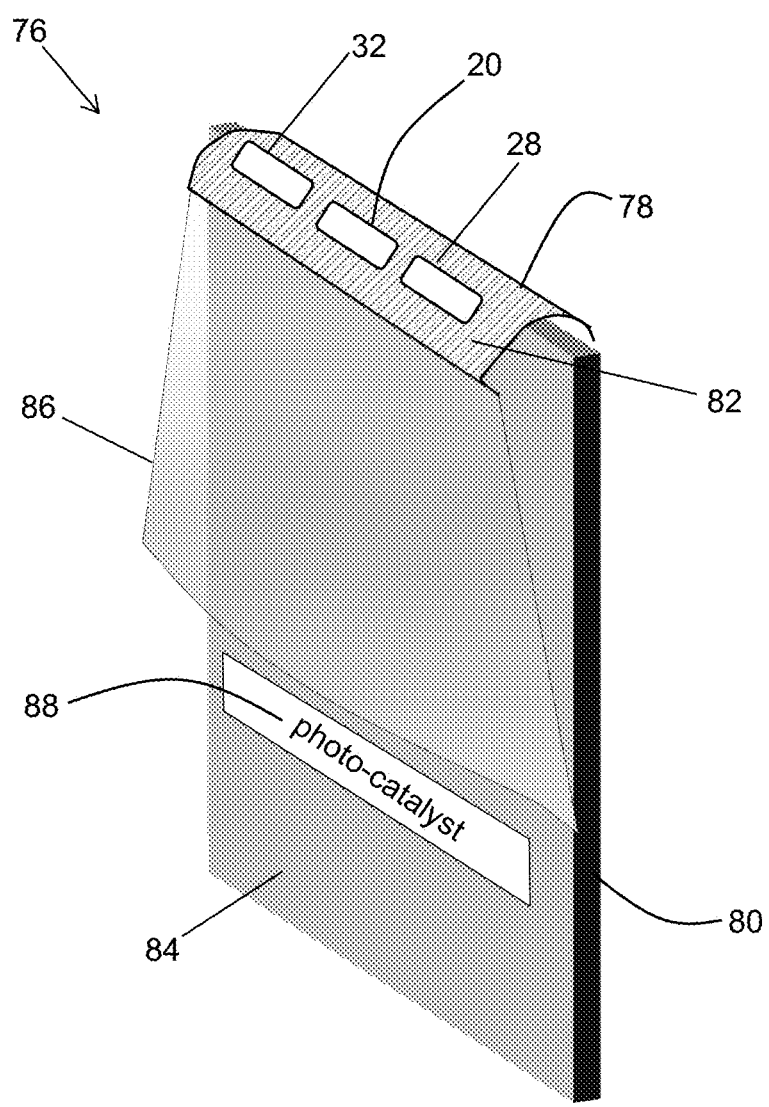
FIG. 7 shows a schematic of a housing for an ultraviolet illuminator that is configured for placement about a walled surface of an aquatic environment according to an embodiment.

FIG. 7 shows a schematic of an ultraviolet illuminator 76 with a housing 78 that is configured for placement about a walled surface 80 of an aquatic environment. In one embodiment, the walled surface 80 of an aquatic environment can include the walls of an aquarium. The housing 78 can be fastened or secured to the walled surface 80 of the aquarium using one of a number well known modalities that include, but are not limited to, clips, binders, screws, bolts, anchors, tabs, springs, etc. In one embodiment, the housing 78 can include an overhang enclosure 82 secured to the walled surface 80 that extends over an inner side 84 of the walled surface 80 that abuts the volume of fluid enclosed by the aquarium. As shown in FIG. 7, the housing 78 can include at least one ultraviolet radiation source 20, at least one sensor 28, and a control unit 32 operatively connected to the ultraviolet radiation source(s) 20 and the sensor(s) 28. The housing 78 including the overhang enclosure 82 can be formed of any of the aforementioned housing materials.

In one embodiment, the ultraviolet radiation source(s) 20, the sensor(s) 28 and the control unit 32 can operate in conjunction with each other to detect the presence of algae or other contaminants that can form on the inner side 84 of the walled surface 80 of the aquarium, and irradiate the walls with ultraviolet radiation 86 to eliminate the algae and/or contaminants and suppress further growth. It is understood that the any of the aforementioned sensors can be used singly or in various combinations to detect conditions that are indicative of the presence of contaminants like algae that can grow on the inner side 84 of the walled surface 80 of the aquarium. Once the control unit 32 determines that the conditions detected by the sensor(s) 28 are indicative of a presence of contaminants like algae that is at a sufficient level (e.g., satisfies a predetermined threshold), then the control unit can direct the ultraviolet radiation source(s) 20 to deliver ultraviolet radiation 86 at the inner side 84 of the walled surface 80. As noted before, the control unit 32, the ultraviolet radiation source(s) 20 and the sensor(s) 28 can operate in conjunction with each other to monitor and manage the irradiation of the inner side 84 of the walled surface until the algae has been removed or suppressed to a level that is not considered to be harmful to the fluid and biota enclosed in the aquarium. In order to facilitate recycling of the ultraviolet radiation 86, the inner side 84 of the walled surface 80 of the aquarium can include a layer, a film or a coating of an ultraviolet reflective material like any of those mentioned previously.

In one embodiment, the irradiation of the inner side 84 of the walled surface 80 in FIG.7 can be enhanced by applying a photocatalyst material 88 to at least a portion of the inner wall. The photocatalyst 88 can enhance the sterilization and disinfection of the inner side 84 of the walled surface 80 upon irradiation by the ultraviolet radiation 86. In particular, the irradiated photocatalyst 88 can undergo a photocatalytic reaction that removes and suppresses algae growth from the inner portion of the walled surface. In one embodiment, the photocatalyst 88 can include $TiO_2$, however, other photocatalysts such as, but not including, metal oxides, such as oxides of vanadium, chromium, titanium, zinc, tin, and cerium, can be used to enhance the sterilization and disinfection of the inner side 84 of the walled surface 80 of an aquatic environment like an aquarium.

Figure 8:
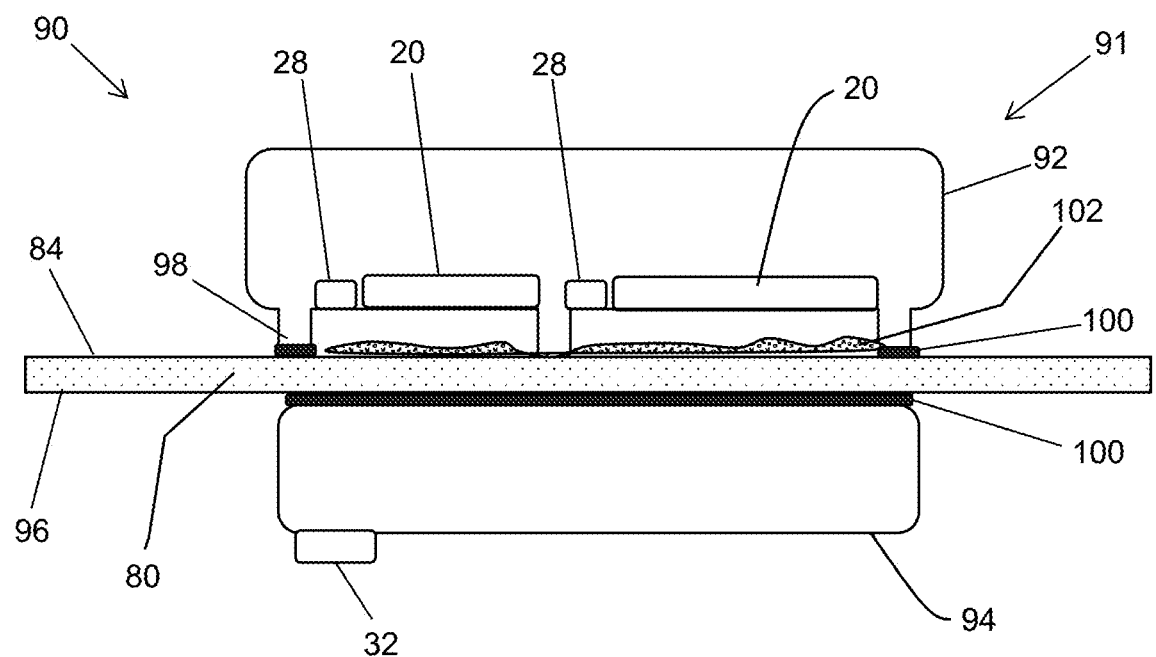
FIG. 8 shows a schematic of an ultraviolet illuminator that is magnetically coupled to a walled surface of an aquatic environment according to an embodiment.
Figure 9:
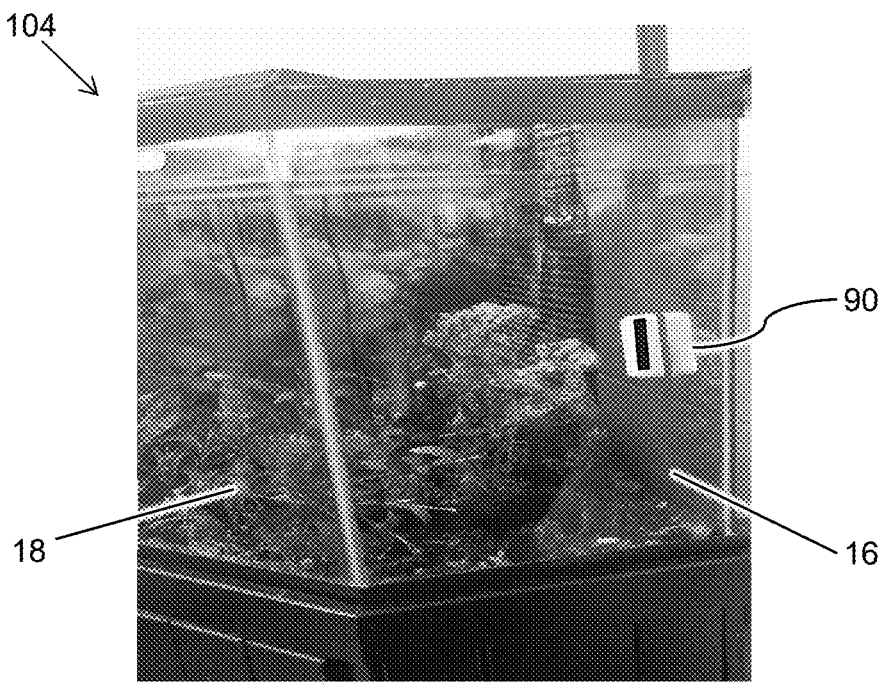
FIG. 9 shows an example of the ultraviolet illuminator depicted in FIG. 8 in use with an aquatic environment such as an aquarium according to an embodiment.

FIG. 8 shows an ultraviolet illuminator 90 having a housing 91 that is configured for magnetic coupling to a portion of a walled surface 80 of an aquatic environment such as an aquarium. An example of the ultraviolet illuminator 90 in use with an aquarium 104 enclosing a body of fluid 16 and biota 18 is shown in FIG. 9, however details of the illuminator is described below with respect to FIG. 8. The housing 91 can include a first magnetic housing section 92 and a second magnetic housing section 94 magnetically coupled to the first magnet housing section 92. As shown in FIG. 8, the first magnetic housing section 92 is separated from the second magnetic housing 94 section by the walled surface 80. In particular, the first magnetic housing section 92 abuts the inner side 84 of the walled surface 80, while the second magnetic housing 94 adjoins an outer side 96 of the walled surface 80. In one embodiment, the first magnetic housing section 92 can include a set of legs 98 that separate the first magnetic housing section 92 from directly touching the glass of the inner side 84 of the walled surface 80 of the aquarium 104.

Both the first magnetic housing section 92 and the second magnetic housing section 94 include a ferromagnetic material 100 that can include, but is not limited to, iron, nickel, cobalt, and the like. In one embodiment, the ferromagnetic material of the first magnetic housing section 92 and the second magnetic housing section 94 can be magnetized with an external magnetic field. In this manner, the first magnetic housing section 92 and the second magnetic housing section 94 can be forced into alignment through magnetic coupling. In one embodiment, the second magnetic housing section 94 can function as a magnetic guide component that is moveable over a portion of the outer side 96 of the walled surface 80. In particular, movement of the magnetic guide component, i.e., the second magnetic housing section 94, in a direction over the outer side 96 of the walled surface 80 facilitates a movement of the first magnetic housing section 92 along the inner side 84 of the walled surface 80 in a corresponding direction with the movement of the second magnetic housing section.

As shown in FIG. 8, the first magnetic housing section 92 can include at least one ultraviolet radiation source 20 to irradiate the inner side 84 of the walled surface 80 of the aquarium 104 to eradicate the presence of any algae or other contaminants 102, while at least one sensor 28 in conjunction with the control unit 32 in the first magnetic housing section 92 can detect the presence the algae. It is understood that the ultraviolet radiation source 20 and the sensor 28 can be deployed with the second magnetic housing section 94. Similarly, the control unit 32 is not meant to be limited to placement with the second magnetic housing section 94. Also, in one embodiment, one of the ultraviolet radiation sources 20 can be oriented to face the fluid 16 enclosed by the walled surface 80 while another source can be oriented to face the inner side 84 of the walled surface 80 to provide greater irradiation coverage of the aquarium. In this manner, sterilization and disinfection is not just limited to irradiating the walled surface. It is understood that the number and position of the ultraviolet radiation sources 20 and the sensors 28 depicted in FIG. 8 is not meant to be limiting, but only to illustrate one of many possible arrangements of these elements.

Like the other embodiments described herein, the ultraviolet radiation source(s) 20, the sensor(s) 28 and the control unit 32 can operate in conjunction with each other to detect the presence of algae or other contaminants that can form on the inner side 84 of the walled surface 80 of the aquarium or in the body of fluid. In addition, the ultraviolet radiation source(s) 20, the sensor(s) 28 and the control unit 32 can facilitate the irradiation of the walls and the fluid with ultraviolet radiation to eliminate the algae and suppress further growth, as well as sterilize and disinfect the fluid. In one embodiment, the control unit 32 can be configured to activate operation of the ultraviolet radiation source(s) in response to the sensor(s) 28 detecting movement of the first magnet housing section 92 and the second magnet housing section 94 over the walled surface 80. During the irradiation, the control unit 32, the ultraviolet radiation source(s) 20 and the sensor(s) 28 can operate in conjunction with each other to monitor and manage the irradiation of the inner side 84 of the walled surface until the algae has been removed or suppressed to a level that is not considered to be harmful to the fluid 16 and biota 18 enclosed in the aquarium 104. Although not shown in FIG. 8, the first magnet housing section 92 can be configured to have a fluid suction and filtering unit for collecting any algae and other contaminants that may be released from the inner side 84 of the walled surface 80 of the aquarium during the cleaning process.

As noted above with regard to FIG. 1, irradiation systems of the various embodiments can utilize a fluid permeable, ultraviolet radiation blocking material 36 to separate the portion of the body of fluid in an aquatic environment into a first section containing only fluid and a second section containing fluid, biota and ornamental objects. In this manner, the ultraviolet radiation source(s) of the ultraviolet illuminator in the systems can irradiate the fluid in the first section for removal of the algae growth or other contaminants, while the fluid permeable, ultraviolet radiation blocking material 36 can prevent the irradiation of the fluid and biota in the second section. As noted above, the fluid permeable, ultraviolet radiation blocking material 36 can be configured to permit the algae or contaminants removed from the first section to pass through and collect at a bottom portion of the aquatic environment in the second section.

Figure 10A:
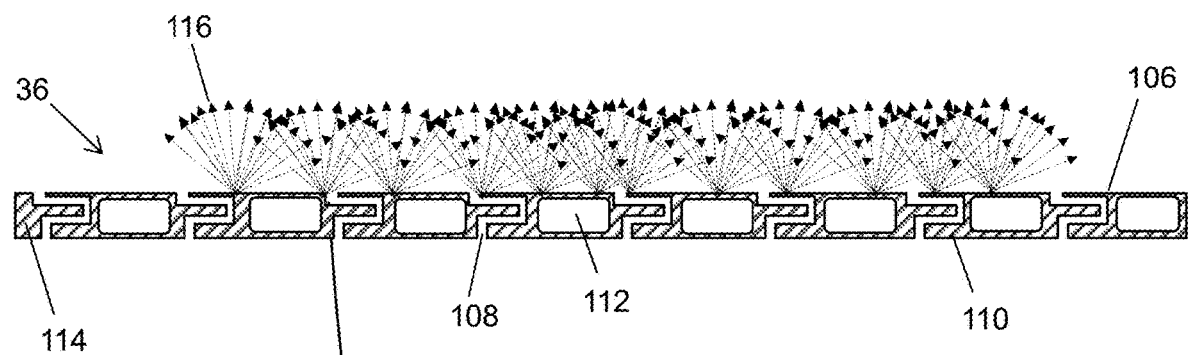
FIGS. 10A-10B show schematic views of a fluid permeable, ultraviolet radiation blocking material configured for placement in the aquatic environment to separate the body of fluid into a first section and a second section according to an embodiment.
Figure 10B:
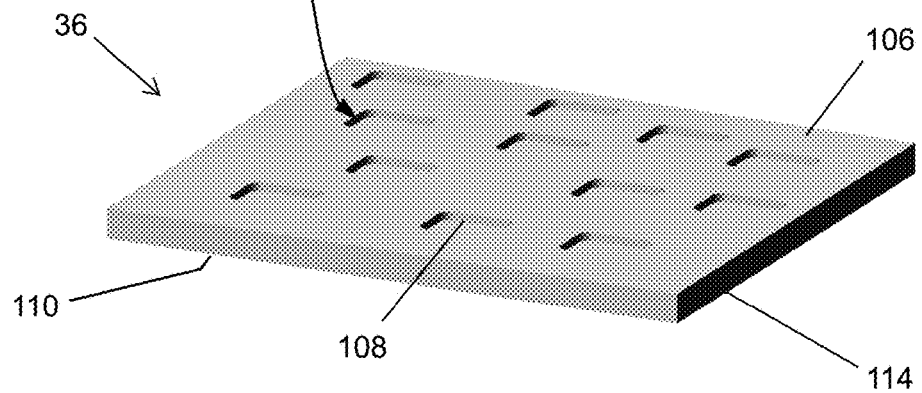

FIGS. 10A-10B show more detailed schematic views of the fluid permeable, ultraviolet radiation blocking material 36 according to an embodiment. As shown in FIGS. 10A-10B, the fluid permeable, ultraviolet radiation blocking material 36 can include a top surface 106 facing the first section of the aquatic environment that only contains fluid and is irradiated by at least one ultraviolet radiation source. A plurality of spaced channels 108 can extend irregularly from the top surface 106 to a bottom surface 110 facing the second section of the aquatic environment that can contain fluid, biota and any ornamental objects. In one embodiment, the spaced channels 108 can extend from the top surface 106 to the bottom surface 110 in a serpentine pattern. It is understood that any other irregularly shaped pattern that can block the transmission of the ultraviolet radiation from traveling from the first section to the second section while still permitting the flow fluid between sections is suitable for use with the fluid permeable, ultraviolet radiation blocking material 36. The fluid permeable, ultraviolet radiation blocking material 36 can include a plurality of spaced voids 112 formed in an internal portion 114 between the top surface 106 and the bottom surface 110. FIG. 10A shows that each void 112 can be formed between a pair of adjacent channels 108 extending from the top surface 106 and the bottom surface 108.

In one embodiment, the fluid permeable, ultraviolet radiation blocking material 36 can include scattering optical elements to facilitate recycling of the radiation generated from the ultraviolet radiation source(s) and increasing the coverage of the radiation. For example, FIG. 10A shows that the top surface 106 of the fluid permeable, ultraviolet radiation blocking material 36 can include a layer, coating or film of ultraviolet reflective material configured to recycle ultraviolet radiation 116 within the first section of the aquatic environment. The layer, coating or film of ultraviolet reflective material can be partially transparent and partially reflective. To this extent, the layer, coating or film of ultraviolet reflective material along with the top surface 106, the channels 108, and the voids 112 form a reflecting unit that can dissipate the ultraviolet radiation generated from the ultraviolet radiation source(s).

Figure 11:
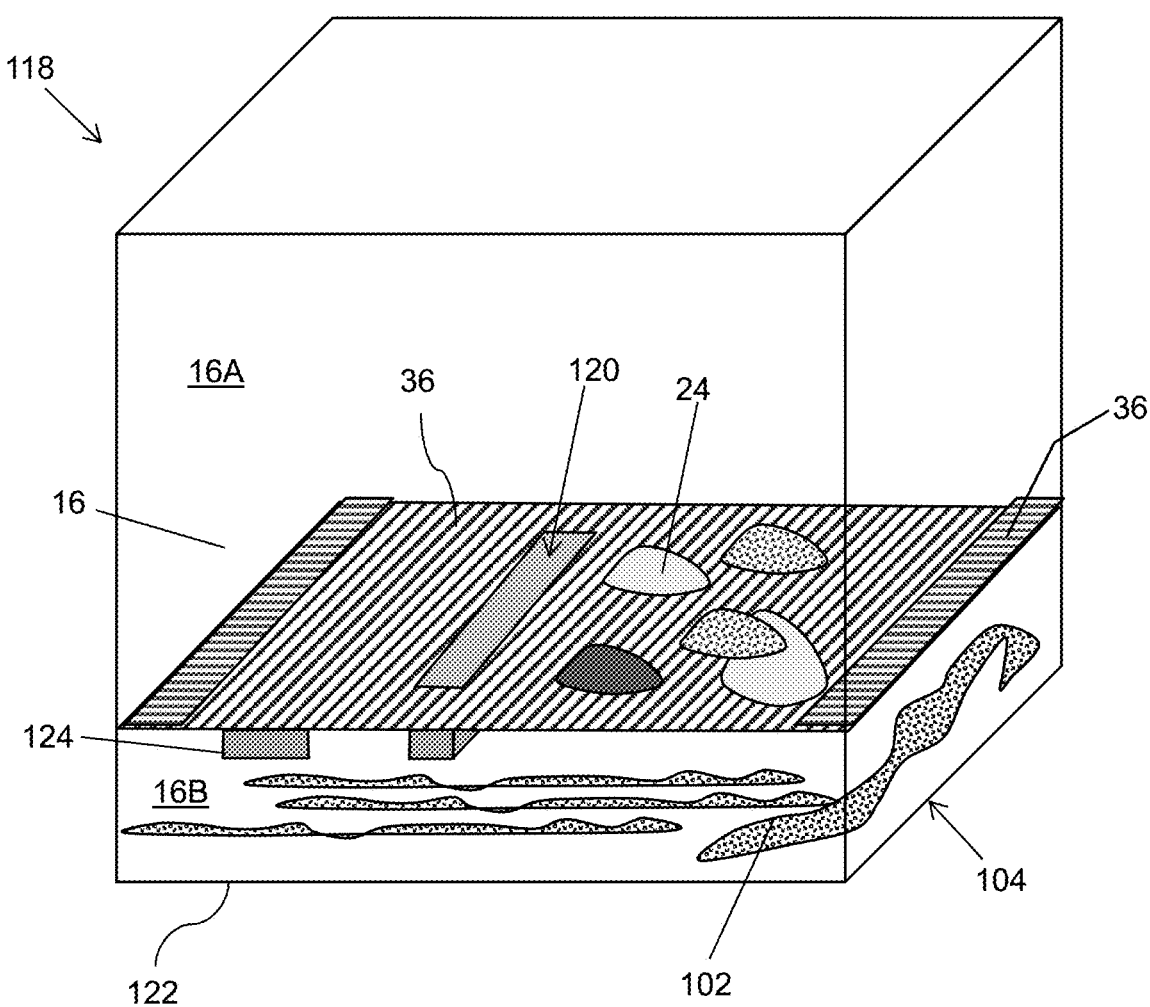
FIG. 11 shows a schematic view of system having an ultraviolet illuminator for irradiating an aquatic environment with a fluid permeable, ultraviolet radiation blocking material that permits the passage of removed algae for collection at the bottom of the aquatic environment according to an embodiment.

FIG. 11 shows a schematic view of system 118 having an ultraviolet illuminator 120 for irradiating an aquatic environment such as an aquarium 104 with a fluid permeable, ultraviolet radiation blocking material 36 that permits the passage of removed algae 102 for collection at the bottom 122 of the aquarium. Although not illustrated in FIG. 11 for purposes of clarity, it is understood that the ultraviolet illuminator 120 can include at least one ultraviolet radiation source and at least one sensor operatively coupled with each other and to a control unit. The ultraviolet illuminator 120 can operate in the manner described above to remove contaminants such as algae from the fluid 16 and the ornamental objects 24 and suppress its capability for further growth. In addition, the ultraviolet illuminator 120 can be configured to sterilize and disinfect the fluid 16 and the walls of the aquarium 104.

As shown in FIG. 11, any algae and contaminants that are removed from a first section of the fluid 16A can transfer to the second section 16B of the fluid through the permeable, ultraviolet radiation blocking material 36. The removed algae and contaminants can collect at the bottom 122 of the aquarium 104. In one embodiment, an ultraviolet radiation source can be located in the section of the aquarium 104 containing the second section 16B of the fluid in order to completely eliminate the existence of the algae 102 from the aquarium. For example, the ultraviolet illuminator 120 can be configured to have an ultraviolet radiation source positioned in the section of the aquarium having the second section 16B of the fluid. In another embodiment, an ultraviolet radiation source can be positioned on the bottom surface of the permeable, ultraviolet radiation blocking material 36 facing the second section 16B of the fluid in order to irradiate algae 102 that has collected at the bottom 122 of the aquarium 104.

It is understood that the system 118 can be implemented with other components that can utilize the ultraviolet radiation generated from any of the ultraviolet radiation sources for purposes that enhance the aquarium 104. For example, a tanning unit 124 can be implemented in the aquarium 104 to attract marine life and irradiate the aquatic species (e.g., fish) with ultraviolet radiation to add more color to the species giving them a more aesthetically pleasing appearance. In one embodiment, the tanning unit 124 can include an enclosure having an entrance, an exit, and a tanning component comprising ultraviolet radiation sources that can deliver ultraviolet radiation at a predetermined intensity and wavelength appropriate for the well-being of the marine life or other living organism that enter the tanning unit 124. Further, the tanning component 124 can be configured to deliver the appropriate ultraviolet radiation dose for a particular duration that has been determined to have no ill effects on the marine life being irradiated.

The irradiation systems of any of the various embodiments described herein can utilize other sources that can aid in the sterilization and disinfection of the aquatic environments, and are not meant to be limited to the use of ultraviolet radiation sources. For example, one or more visible light sources can be configured to irradiate the fluid in an aquatic environment with visible light radiation and operate in conjunction with the ultraviolet radiation source(s). In one embodiment, the visible light from the visible light emitting source can complement the ultraviolet radiation source(s) in removing the algae growth and suppressing further algae growth. Examples of visible light sources that can be used include, but are not limited to, visible light emitting diodes, fluorescent lights, compact fluorescent lights, neon lights, incandescent lights, etc. In one embodiment, a set of blue and visible light emitting diodes can be used with the ultraviolet radiation sources.

Any implementation of the ultraviolet radiation source(s) with or without the visible light sources, and the sensor(s) is not meant to be limited to one specific configuration as a multiple of arrangements of these components is possible. This multiple of arrangements can include varying positional locations of these components within the aquatic environment with respect to the fluid and any surfaces encompassing the fluid. Similarly, the number of each of the components that are utilized in an arrangement is variable. Further, the components can be configured to function in a coordinated manner or an uncoordinated manner. For example, some ultraviolet radiation sources 20 can operate at the same wavelengths and intensities for the same duration, or the sources can operate at different wavelengths and intensities for varying durations. In one embodiment, a first set of ultraviolet radiation sources 20 can operate at a target wavelength and intensity that is designed for the sterilization of algae, and a second set of ultraviolet radiation sources can operate at a different target wavelength and intensity that is designed for disinfection of a particular type of bacteria and/or virus. In one embodiment, the ultraviolet radiation sources 20 can be arranged in a distributed arrangement throughout the aquatic environment. In this manner, the control unit 32 can activate a particular set of ultraviolet radiation sources 20 that are in proximity to a specific area determined to have unacceptable levels of algae growth and direct those sources to irradiate the area until the algae has been eliminated. In one embodiment, a set of ultraviolet radiation sources 20 that are directed to irradiate a particular area of the aquatic environment can be configured to operate in an intermittent manner until it has been determined that the levels of algae have reached an acceptable target value.

Figure 12:
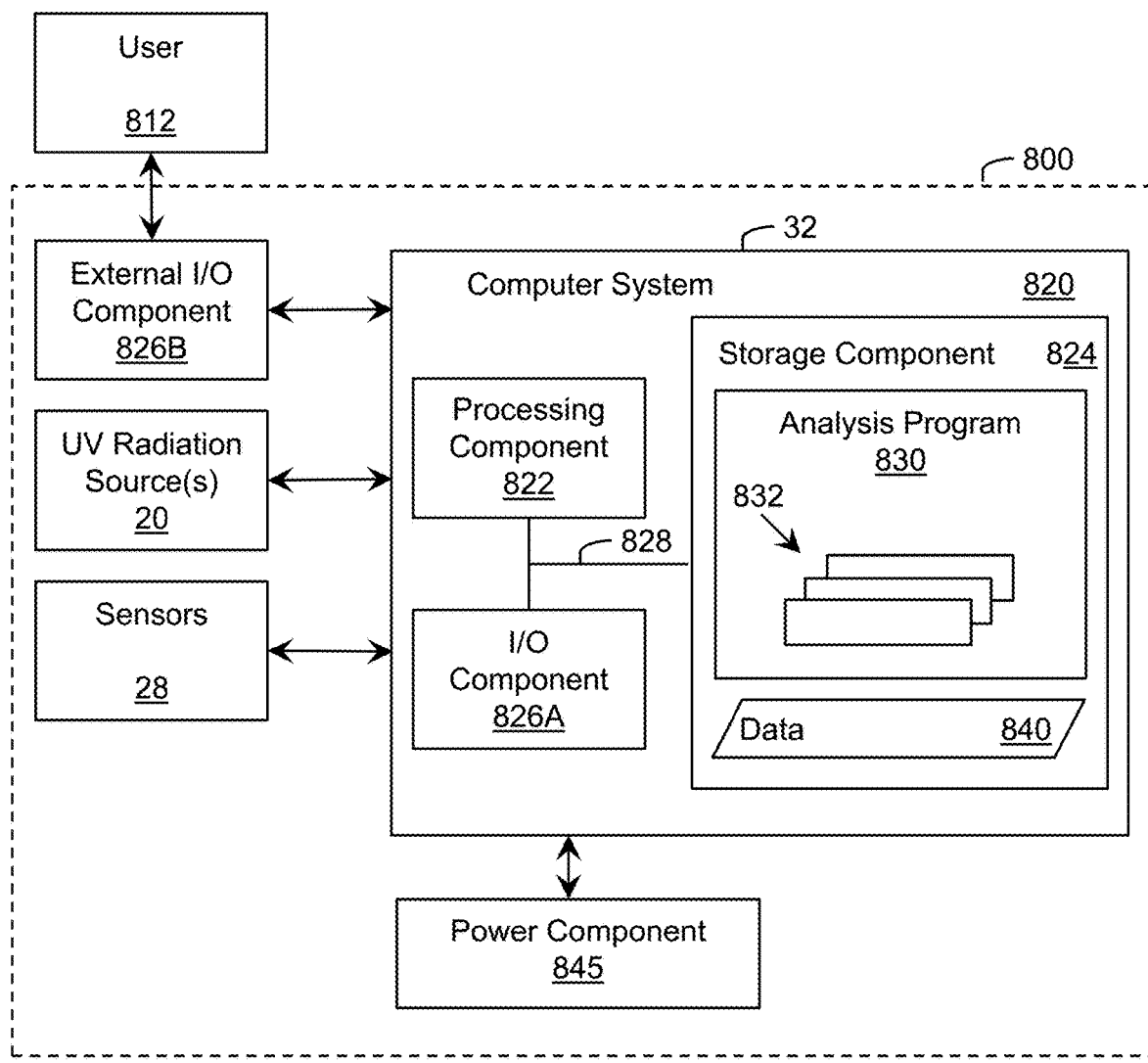
FIG. 12 shows a schematic block diagram representative of an overall processing architecture of a system utilizing an ultraviolet illuminator for irradiating an aquatic environment that is applicable to any of the systems described herein according to an embodiment.

FIG. 12 shows a schematic block diagram representative of an overall processing architecture of a system 800 utilizing an ultraviolet illuminator for irradiating an aquatic environment that is applicable to any of the systems described herein. In this embodiment, the architecture 800 is shown including the ultraviolet radiation sources 20 (UV radiation source(s)) and the sensors 28 for the purposes of illustrating the interaction of all of the components that can be used to provide an ultraviolet treatment of an aquatic environment.

As depicted in FIG. 12 and described herein, the system 800 can include a control unit 32. In one embodiment, the control unit 32 can be implemented as a computer system 820 including an analysis program 830, which makes the computer system 820 operable to manage the ultraviolet radiation sources 20 and the sensors 28 in the manner described herein. In particular, the analysis program 830 can enable the computer system 820 to operate the ultraviolet radiation sources 20 to generate and direct ultraviolet radiation towards the aquatic environment and process data corresponding to one or more attributes regarding the fluid and surfaces of the aquatic environment which can be acquired by the sensors 28. The computer system 820 can individually control each ultraviolet radiation source 20 and sensor 28 and/or control two or more of the ultraviolet radiation sources and the sensors as a group. Furthermore, the ultraviolet radiation sources 20 can emit ultraviolet radiation of substantially the same wavelength or of multiple distinct wavelengths, or at any other noted sets of peak wavelengths.

In an embodiment, during an initial period of operation, the computer system 820 can acquire data from at least one of the sensors 20 regarding one or more attributes of the fluid and surfaces of the aquatic environment and generate data 840 for further processing. The data 840 can include information regarding a presence of biological activity (e.g., microorganisms, viruses, bacteria, and/or the like) in the fluid and surfaces, an amount of radiation (e.g., ultraviolet, infrared, visible, and/or microwave) detected, and/or the like. The computer system 820 can use the data 840 to control one or more aspects of the ultraviolet radiation generated by the ultraviolet radiation source(s) 20 during an ultraviolet treatment.

Furthermore, one or more aspects of the operation of the ultraviolet radiation sources 20 can be controlled or adjusted by a user 812 via an external interface I/O component 826B. The external interface I/O component 826B can be located, for example, on the exterior of any of the aforementioned illuminators and used to allow the user 812 to selectively turn on/off the ultraviolet radiation sources 20.

The external interface I/O component 826B can include, for example, a touch screen that can selectively display user interface controls, such as control dials, which can enable the user 812 to adjust one or more of: an intensity, scheduling, and/or other operational properties of the set of ultraviolet radiation sources 20 (e.g., operating parameters, radiation characteristics). In an embodiment, the external interface I/O component 826B could conceivably include a keyboard, a plurality of buttons, a joystick-like control mechanism, and/or the like, which can enable the user 812 to control one or more aspects of the operation of the set of ultraviolet radiation sources 20. The external interface I/O component 826B also can include any combination of various output devices (e.g., an LED, a visual display), which can be operated by the computer system 820 to provide status information pertaining to a treatment of an aquatic environment for use by the user 812. For example, the external interface I/O component 826B can include one or more LEDs for emitting a visual light for the user 812, e.g., to indicate a status of the ultraviolet treatment. In an embodiment, the external interface I/O component 826B can include a speaker for providing an alarm (e.g., an auditory signal), e.g., for signaling that ultraviolet radiation is being generated or that an ultraviolet treatment has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the ultraviolet radiation sources and the sensors. To this extent, in other embodiments, the functionality provided by the computer system 820 and the analysis program 830 can be at least partially implemented by one or more computing devices that include any combination of general and/or specific purpose hardware with or without program code. In each embodiment, the hardware and program code, if included, can be created using standard engineering and programming techniques, respectively. In another embodiment, the control unit can be implemented without any computing device, e.g., using a closed loop circuit implementing a feedback control loop in which the outputs of one or more sensors are used as inputs to control the operation of a treatment. Illustrative aspects of the invention are further described in conjunction with the computer system 820. However, it is understood that the functionality described in conjunction therewith can be implemented by any type of monitoring and/or control system.

When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent computer systems that may perform a process described herein. To this extent, in other embodiments, the functionality provided by the computer system 820 and the analysis program 830 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 820 includes multiple computing devices, the computing devices can communicate over any type of communications link. Furthermore, while performing a process described herein, the computer system 820 can communicate with one or more other computer systems using any type of communications link. In either case, the communications link can comprise any combination of various types of wired and/or wireless links; any combination of one or more types of networks; and/or utilize any combination of various types of transmission techniques and protocols.

All of the components depicted in FIG. 12 can receive power from a power component 845. The power component 845 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power component can include solar, a mechanical energy to electrical energy converter such as a piezoelectric crystal, a rechargeable device, etc.

While shown and described herein as a system and method, it is understood that aspects of the present invention further provide various alternative embodiments. For example, in one embodiment, the various embodiments of the present invention can include a computer program fixed in at least one computer-readable medium, which when executed, enables a computer system to facilitate the ultraviolet irradiation of fluids. To this extent, the computer-readable medium includes program code, such as the analysis program 830, which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the present invention can provide a method of providing a copy of program code, such as the analysis program 830, which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the present invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the various embodiments of the present invention can implement a method that facilitates the ultraviolet irradiation of fluids. This can include configuring a computer system, such as the computer system 820, to implement a method for facilitating the ultraviolet irradiation of fluids. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. An ultraviolet illuminator for treating an aquatic environment having a body of fluid interacting with biota, comprising:
   at least one ultraviolet radiation source configured to irradiate the aquatic environment;
   at least one sensor to detect conditions of the aquatic environment including fluid conditions and/or surface conditions associated with the aquatic environment; and
   a control unit, operatively coupled to the at least one ultraviolet radiation source and the at least one sensor, wherein the control unit is configured to determine a presence of algae growth about the aquatic environment and whether the presence of algae growth warrants irradiation by the at least one ultraviolet radiation source, wherein the control unit ascertains whether the presence of algae growth has an algae density with a rate of change that exceeds a predetermined maximum rate, wherein the control unit directs the at least one ultraviolet radiation source to irradiate the aquatic environment with ultraviolet radiation at locations where there is a presence of algae growth with an algae density having a rate of change that exceeds the predetermined maximum rate for removal thereof and suppression of further algae growth, wherein the control unit monitors the irradiation of the aquatic environment with the ultraviolet radiation with the at least one sensor, and adjusts irradiation parameters of the at least one ultraviolet radiation source as a function of conditions detected by the at least one sensor, wherein the control unit is configured to direct the at least one ultraviolet radiation source to stop irradiating the locations in the aquatic environment in response to determining that the rate of change of the algae density is below a predetermined minimum level.

2. The ultraviolet illuminator of claim 1, further comprising a housing that encloses the at least one ultraviolet radiation source and the at least one sensor, wherein the housing is configured for placement in a plurality of locations about the aquatic environment.

3. The ultraviolet illuminator of claim 2, wherein the housing is immersible within the body of fluid.

4. The ultraviolet illuminator of claim 3, wherein the housing comprises a chamber, an inlet for permitting passage of fluid into the chamber and an outlet for permitting passage of the fluid out from the chamber.

5. The ultraviolet illuminator of claim 4, wherein the at least one ultraviolet radiation source comprises a plurality of ultraviolet radiation sources and the at least one sensor comprises a plurality of sensors, and wherein the plurality of ultraviolet radiation sources and the plurality of sensors are located about the chamber.

6. The ultraviolet illuminator of claim 5, wherein the plurality of sensors comprise an ultraviolet radiation sensor and a fluorescent sensor, wherein the ultraviolet radiation sensor is configured to detect ultraviolet intensity in the fluid in the chamber after entering the inlet and being irradiated by a first ultraviolet radiation source, and the fluorescent sensor is configured to detect fluorescent illumination intensity of the fluid in the chamber after being irradiated by a second ultraviolet radiation source before exiting through the outlet.

7. The ultraviolet illuminator of claim 6, wherein the control unit is configured to determine a fluid transparency of the fluid in the chamber as a function of the detected ultraviolet intensity in the fluid, and an algae density level within the fluid as a function of the detected fluorescent illumination intensity.

8. The ultraviolet illuminator of claim 7, wherein the control unit is configured to activate operation of the plurality of ultraviolet radiation sources if the algae density level satisfies a first predetermined threshold, wherein the control unit is configured to manage the irradiation of the fluid by monitoring conditions of the fluid during irradiation and adjust the irradiation parameters of the plurality of ultraviolet radiation sources as a function of the detected ultraviolet intensity in the fluid and the detected fluorescent illumination intensity.

9. The ultraviolet illuminator of claim 5, wherein one of the plurality of sensors comprises a chemical sensor configured to detect chemical components within the fluid.

10. The ultraviolet illuminator of claim 9, wherein the chemical sensor comprises a conduit fluidly coupled to a port within the chamber, a vessel for receiving a sample of fluid from the chamber by the conduit, and a chemical component detector to detect the chemical components of the fluid in the vessel.

11. The ultraviolet illuminator of claim 9, wherein the control unit is configured to determine a pH balance and a chlorine level in the fluid as a function of the detected chemical components.

12. The ultraviolet illuminator of claim 11, wherein the control unit is configured to activate operation of the plurality of ultraviolet radiation sources if the pH balance and the chlorine level in the fluid satisfies a second predetermined threshold, wherein the control unit is configured to manage the irradiation of the fluid by monitoring conditions of the fluid during the irradiation and adjust the irradiation parameters of the plurality of ultraviolet radiation sources as a function of the determined pH balance and the chlorine level in the fluid.

13. A system, comprising:
   an aquatic environment having a body of fluid interacting with biota and a walled surface that defines an area encompassing the body of fluid and the biota; and
   an ultraviolet illuminator for treating the aquatic environment, the ultraviolet illuminator comprising:
   a housing configured for placement in a plurality of locations about the aquatic environment;
   a set of ultraviolet radiation sources located about the housing to irradiate the aquatic environment, wherein at least one ultraviolet radiation source irradiates the aquatic environment with ultraviolet radiation to determine a presence of algae growth;
  a set of sensors to detect conditions of the aquatic environment including fluid conditions and/or surface conditions associated with the aquatic environment, wherein at least one sensor obtains data from the aquatic environment in response to irradiation by the at least one ultraviolet radiation source, wherein the data is related to the algae growth in the aquatic environment and is a function of the ultraviolet radiation emitted from the at least one ultraviolet radiation source; and
  a control unit, operatively coupled to the set of ultraviolet radiation sources and the set of sensors, wherein the control unit is configured to determine the presence of algae growth about the aquatic environment from the data obtained by the at least one sensor and whether the presence of algae growth warrants further irradiation by the set of ultraviolet radiation sources, wherein the control unit directs the set of ultraviolet radiation sources to irradiate the aquatic environment with additional ultraviolet radiation at locations where there is a presence of algae growth with an algae density having a rate of change that exceeds a predetermined maximum rate for removal thereof and suppression of further growth, wherein the control unit monitors the irradiation of the aquatic environment with the additional ultraviolet radiation with the set of sensors, and adjusts irradiation parameters of the set of ultraviolet radiation sources as a function of conditions detected by the set of sensors, wherein the control unit is configured to direct the set of ultraviolet radiation sources to stop irradiating the locations in the aquatic environment with additional ultraviolet radiation in response to determining that the rate of change of the algae density is below a predetermined minimum level.

14. The system of claim 13, wherein an inner portion of the walled surface of the aquatic environment comprises a photocatalyst material, wherein one of the ultraviolet radiation sources from the set of ultraviolet radiation sources is configured to irradiate the photocatalyst material, the irradiated photocatalyst material undergoing a photocatalytic reaction that removes and suppresses algae growth from the inner portion of the walled surface.

15. The system of claim 13, wherein the housing is magnetically coupled to a portion of the walled surface of the aquatic environment, wherein the housing comprises a first magnetic housing section and a second magnetic housing section magnetically coupled to the first magnet housing section, the first magnetic housing section separated from the second magnetic housing section by the walled surface.

16. The system of claim 15, wherein the set of sensors are located in the first magnetic housing section and the set of ultraviolet radiation sources are located in at least one of the first magnetic housing section and the second magnetic housing section, and wherein the second magnetic housing section includes a magnetic guide component that is moveable over an outer portion of the walled surface, wherein movement of the magnetic guide component in a direction over the outer portion of the walled surface facilitates movement of the first magnetic housing section along the inner portion of the walled surface in a corresponding direction.

17. The system of claim 13, wherein the set of ultraviolet radiation sources are configured to direct ultraviolet radiation towards an inner portion of the walled surface for removal of algae and suppression of further algae growth and/or direct ultraviolet radiation to the body of fluid.

18. The system of claim 16, wherein the control unit is configured to activate operation of the set of ultraviolet radiation sources in response to one of the sensors from the set of sensors detecting movement of the first magnet housing section and the second magnet housing section.

19. A system, comprising:
  an aquatic environment having a body of fluid interacting with biota and a walled surface that defines an area encompassing the body of fluid and the biota;
  an ultraviolet illuminator for treating the aquatic environment, the ultraviolet illuminator comprising:
    a housing configured for placement in a plurality of locations about the aquatic environment;
    a set of ultraviolet radiation sources located about the housing to irradiate the aquatic environment;
    a set of sensors to detect conditions of the aquatic environment including fluid conditions and/or surface conditions associated with the aquatic environment, wherein at least one of the set of sensors comprises a visible camera configured to obtain images from various locations about the aquatic environment; and
  a control unit, operatively coupled to the set of ultraviolet radiation sources and the set of sensors, wherein the control unit is configured to determine a presence of algae growth about the aquatic environment by comparing images from each of the locations obtained by the visible camera over different times, direct the set of ultraviolet radiation sources to irradiate aquatic environment at locations where there is a presence of algae growth for removal thereof and suppression of further growth, monitor the irradiation of the aquatic environment with the visible camera, and adjust irradiation parameters of the set of ultraviolet radiation sources as a function of conditions detected by the visible camera; and
  a fluid permeable, ultraviolet radiation blocking material configured for placement in the aquatic environment in a portion of the body of fluid, the fluid permeable, ultraviolet radiation blocking material separating the portion of the body of fluid into a first section containing only fluid and a second section containing fluid and biota, wherein the set of ultraviolet radiation sources are configured to irradiate the fluid in the first section for removal of the algae growth, while the fluid permeable, ultraviolet radiation blocking material prevents the irradiation of the fluid and biota in the second section, and permits the algae removed from the first section to pass through and collect at a bottom portion of the second section.

20. The system of claim 19, wherein the fluid permeable, ultraviolet radiation blocking material comprises a top surface facing the first section, a bottom surface facing the second section, a plurality of spaced channels each extending irregularly from the top surface to the bottom surface, permitting a flow of fluid including removed algae between the first section and the second section, and a plurality of spaced voids formed in an internal portion between the top surface and the bottom surface, each void formed between a pair of adjacent channels extending from the top surface and the bottom surface.

* * * * *